(12) United States Patent
Kim et al.

(10) Patent No.: US 12,377,268 B2
(45) Date of Patent: Aug. 5, 2025

(54) ARTIFICIAL INTELLIGENCE NEUROFEEDBACK-BASED TELEMEDICINE SYSTEM AND METHOD OF OPERATING THE SAME

(71) Applicant: Korea University Research and Business Foundation, Seoul (KR)

(72) Inventors: Dong Joo Kim, Seoul (KR); Young Tak Kim, Nonsan-si (KR); Hyun Ji Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 478 days.

(21) Appl. No.: 18/008,311

(22) PCT Filed: Jun. 11, 2021

(86) PCT No.: PCT/KR2021/007340
§ 371 (c)(1),
(2) Date: Dec. 5, 2022

(87) PCT Pub. No.: WO2021/251797
PCT Pub. Date: Dec. 16, 2021

(65) Prior Publication Data
US 2023/0200730 A1    Jun. 29, 2023

(30) Foreign Application Priority Data

Jun. 12, 2020  (KR) .................. 10-2020-0071653
Aug. 28, 2020  (KR) .................. 10-2020-0109674
(Continued)

(51) Int. Cl.
*A61N 1/36* (2006.01)
*A61B 5/00* (2006.01)
(Continued)

(52) U.S. Cl.
CPC ...... *A61N 1/36031* (2017.08); *A61B 5/02405* (2013.01); *A61B 5/291* (2021.01);
(Continued)

(58) Field of Classification Search
None
See application file for complete search history.

(56) References Cited

U.S. PATENT DOCUMENTS

2005/0154426 A1    7/2005  Boveja et al.
2013/0238047 A1    9/2013  Libbus et al.
(Continued)

FOREIGN PATENT DOCUMENTS

KR  10-2015-0011154 A    1/2015
KR  10-2017-0132277 A    12/2017
(Continued)

*Primary Examiner* — Ankit D Tejani
(74) *Attorney, Agent, or Firm* — NSIP Law

(57) ABSTRACT

The telemedicine system includes a gateway for transmitting monitoring information including a stimulation signal and a biosignal corresponding to the stimulation signal to a cloud; and a server for extracting the stimulation signal and the biosignal from the transmitted monitoring information, providing the extracted stimulation signal and biosignal as inputs of a pre-stored artificial intelligence machine learning algorithm-based stimulation control model, regenerating the biosignal as an output of the stimulation control model into a stimulation signal to be regulated for the balance between sympathetic and parasympathetic nerves, and feeding back the regenerated stimulation signal to a personalized vagus nerve stimulation and pulse electromagnetic field treatment device.

18 Claims, 13 Drawing Sheets

(30) Foreign Application Priority Data

Aug. 28, 2020 (KR) .......................... 10-2020-0109680
Aug. 28, 2020 (KR) .......................... 10-2020-0109683
Aug. 28, 2020 (KR) .......................... 10-2020-0109689

(51) Int. Cl.
   *A61B 5/024* (2006.01)
   *A61B 5/291* (2021.01)
   *A61N 1/04* (2006.01)

(52) U.S. Cl.
   CPC .......... *A61B 5/4035* (2013.01); *A61B 5/4836* (2013.01); *A61B 5/68* (2013.01); *A61B 5/7264* (2013.01); *A61N 1/0456* (2013.01); *A61N 1/36025* (2013.01); *A61N 1/36053* (2013.01)

(56) References Cited

U.S. PATENT DOCUMENTS

2019/0046794 A1* 2/2019 Goodall ............. A61N 1/36014
2019/0313934 A1* 10/2019 Lee ..................... A61B 5/0002

FOREIGN PATENT DOCUMENTS

| KR | 10-2006962 B1 | 7/2019 |
| KR | 10-2019-0099006 A | 8/2019 |
| KR | 10-2019-0101633 A | 9/2019 |
| KR | 10-2020-0035053 A | 4/2020 |

* cited by examiner

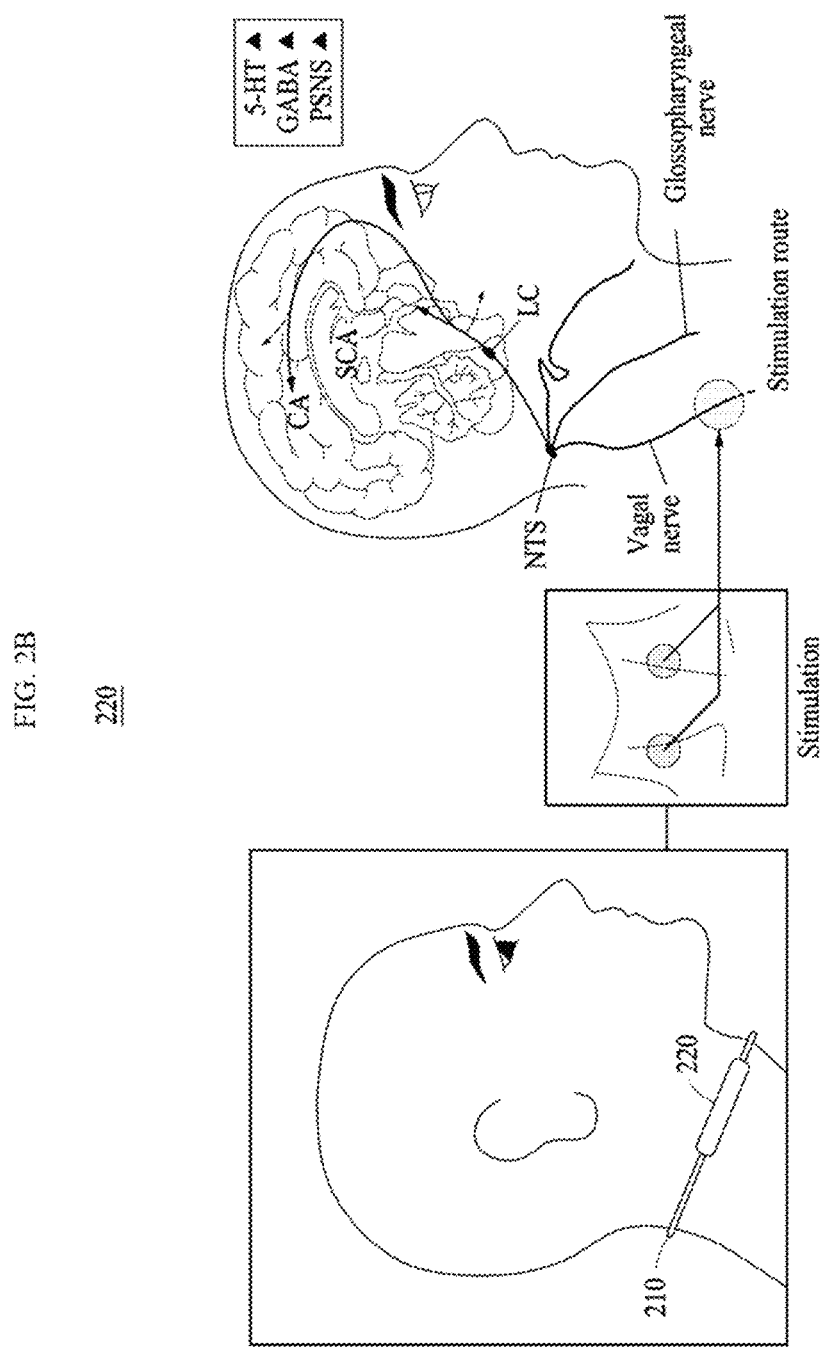

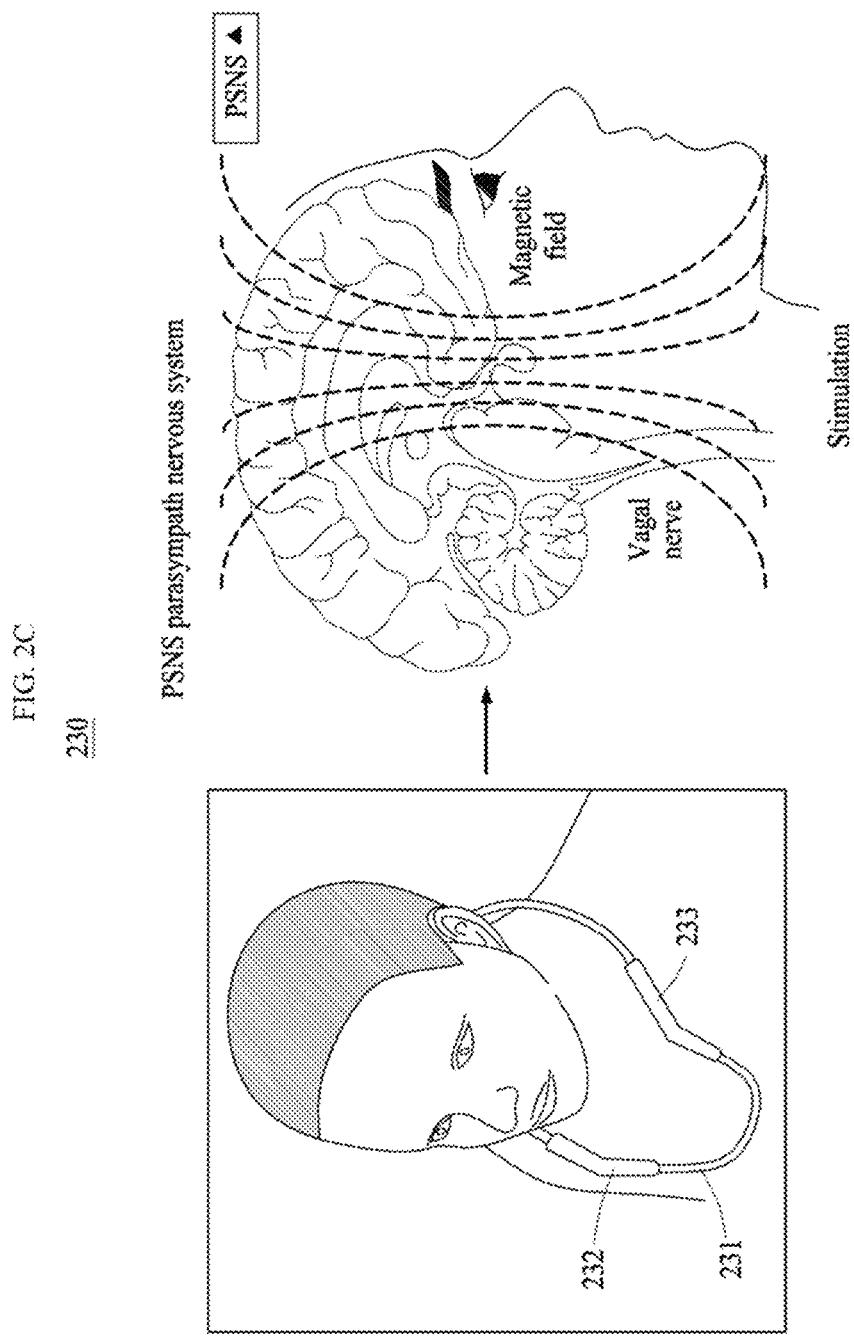

300

400

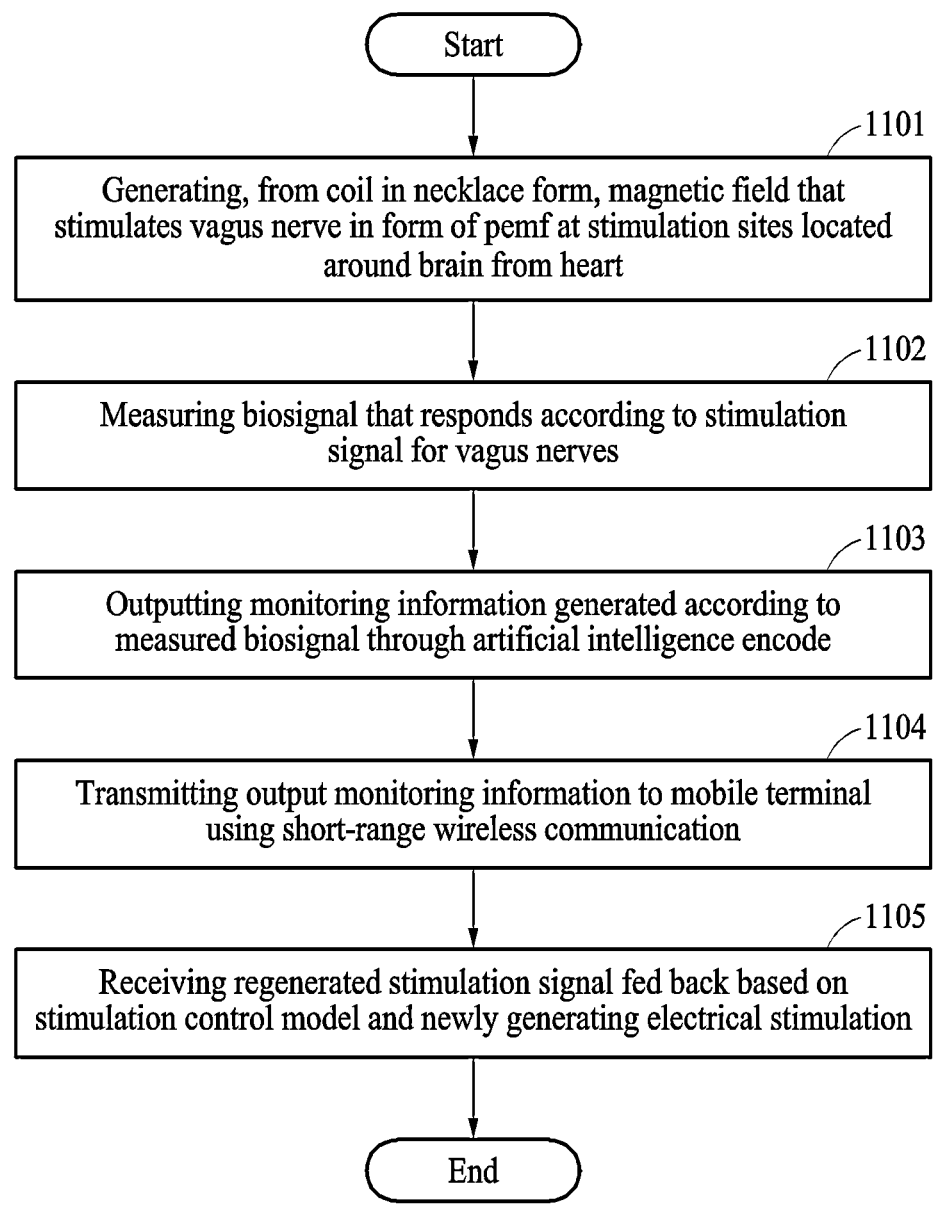

ARTIFICIAL INTELLIGENCE NEUROFEEDBACK-BASED TELEMEDICINE SYSTEM AND METHOD OF OPERATING THE SAME

CROSS REFERENCE TO RELATED APPLICATIONS

This application is a U.S. National Stage Application of International Application No. PCT/KR2021/007340 filed on Jun. 11, 2021, which claims the benefit under 35 USC 119 (a) and 365(b) of Korean Patent Application No. 10-2020-0071653, filed on Jun. 12, 2020, Korean Patent Application No. 10-2020-0109674, filed on Aug. 28, 2020, Korean Patent Application No. 10-2020-0109680, filed on Aug. 28, 2020, Korean Patent Application No. 10-2020-0109683, filed on Aug. 28, 2020, and Korean Patent Application No. 10-2020-0109689, filed on Aug. 28, 2020, in the Korean Intellectual Property Office, the entire disclosures of which are incorporated herein by reference for all purposes.

TECHNICAL FIELD

The present invention relates to a telemedicine technique in which vagus nerves are stimulated in the form of cranial electrotherapy stimulation (CES), transcutaneous electrical nerve stimulation (TENS), or a pulsed electromagnetic field (PEMF) and user-specific responses are reflected using artificial intelligence to alleviate diseases or related symptoms caused by an imbalance between sympathetic and parasympathetic nerves.

BACKGROUND ART

Anxiety disorders are characterized by excessive anxiety and apprehension lasting for 6 months or more and accompanied by various physical symptoms such as fatigue, tremor, and anxiety. In general, anxiety disorders are primarily caused by abnormalities in neurotransmitters or by defects in neural inhibition and serotonin regulation by gamma-aminobutyric acid (GABA) in cranial nerves responsible for emotional feelings such as anxiety and depression.

GABA is a major inhibitory neurotransmitter and exerts inhibitory or modulatory effects on norepinephrine. When GABA binds to GABA receptors, chloride ion channels are opened and negatively charged chloride ions flow in, reducing excitability of neurons.

In addition, serotonin is an inhibitory neurotransmitter widely diffused in areas of the brain such as the amygdala, hippocampus, and limbic system. When serotonin is increased, the activity of norepinephrine is reduced, and defense and avoidance responses are inhibited.

The major symptoms accompanying anxiety disorders include sleep disturbance, panic, and migraine. The main symptoms of anxiety disorders are detailed below.

First, sleep disturbance results from a decrease in serotonin, and serotonin is used as a raw material for melatonin, which is known as a sleep hormone. When serotonin is reduced, melatonin is also reduced, and thus causes sleep disturbance.

When GABA is reduced, brain activity does not stop due to lack of GABA in the brain, causing wakefulness and disrupting sleep.

In addition, panic is caused by a decrease in serotonin. Lack of serotonin weakens the dopamine inhibitory function of the locus coeruleus and raphe nuclei in the midbrain and cerebral medulla.

When GABA is reduced, lack of GABA may act against excitatory neurotransmitters that stimulate the brain, weakening the stabilizing role thereof in the central nervous system.

In addition, migraine is mainly caused by a decrease in serotonin. Specifically, migraine may occur because the brain cannot suppress nociceptive information input from the periphery due to a lack of serotonin in the descending pain suppression system.

According to conventional methods, the above symptoms due to an imbalance between sympathetic and parasympathetic nerves are treated using drugs or a vagus nerve stimulator without considering the user's condition.

However, in the case of drug treatment, serious side effects such as muscle spasm or suicidal ideation may occur in the case of overdose or misuse. In particular, in the case of benzodiazepine drugs, there is a risk of addiction. Accordingly, most of the drugs for treating these diseases require a hospital prescription, which limits the use thereof.

In addition, the vagus nerve stimulator without considering the user's condition may cause serious side effects such as headache and swallowing disorder due to stimulation control dependent on the user's subjectivity.

In addition, persistent stimulation through a single pathway may damage nerves. In addition, when the vagus nerves are directly stimulated, side effects of surgery may be serious.

Therefore, novel technology that may implement relief of diseases or related symptoms caused by an imbalance between sympathetic and parasympathetic nerves, correction of overactivation of sympathetic nerves due to chronic pain/stress and mood disorders, and activation of the parasympathetic nervous system for mental and physical stability needs to develop.

DISCLOSURE

Technical Problem

Therefore, the present invention has been made in view of the above problems, and it is one object of the present invention to provide a personalized medical service capable of managing symptoms anytime, anywhere based on artificial intelligence-based personalized biofeedback through digital therapeutics during daily life.

It is another object of the present invention to provide a telemedicine service delivery system in preparation for the post-corona era.

It is still another object of the present invention to monitor an autonomic nervous system response, eliminate subjective processing through artificial intelligence stimulation feedback based on the autonomic nervous system response, and provide a stimulation recipe optimized for a user.

It is still another object of the present invention to alleviate sleep disturbance, emotional disturbance, and digestive symptoms caused by an imbalance of sympathetic and parasympathetic nerves by inducing release of inhibitory neurotransmitters including GABA, serotonin, and norepinephrine in the central nervous system through stimulation of vagus nerves.

It is still another object of the present invention to alleviate diseases or related symptoms caused by an imbalance between sympathetic and parasympathetic nerves.

It is still another object of the present invention to correct overactivation of sympathetic nerves due to chronic pain/stress and affective disorders.

It is still another object of the present invention to overcome the limitations of conventional vagus nerve stimulators provided based on manuals through personalized vagus nerve stimulation optimization using an artificial intelligence algorithm.

It is still another object of the present invention to activate the parasympathetic nervous system for body and mind relaxation.

It is yet another object of the present invention to alleviate low back pain, pelvic pain, neuropathic pain, and neuralgia/myalgia and increase the treatment effect of fractures by enhancing metabolism of fibroblasts, chondrocytes, and osteoblasts through magnetic field stimulation and modulating the effects of hormones and neurotransmitters on the receptors of various cells.

Technical Solution

In accordance with one aspect of the present invention, provided is a telemedicine system including a gateway for transmitting monitoring information including a stimulation signal and a biosignal corresponding to the stimulation signal to a cloud; and a server for extracting the stimulation signal and the biosignal from the transmitted monitoring information, providing the extracted stimulation signal and biosignal as inputs of a pre-stored artificial intelligence machine learning algorithm-based stimulation control model, regenerating the biosignal as an output of the stimulation control model into a stimulation signal to be regulated for balance between sympathetic and parasympathetic nerves, and feeding back the regenerated stimulation signal to a personalized vagus nerve stimulation and pulse electromagnetic field treatment device, wherein the monitoring information includes a biosignal measured when vagus nerves are stimulated in a form of electromagnetism at a stimulation site based on a stimulation signal generated from the personalized vagus nerve stimulation and pulse electromagnetic field treatment device, and the personalized vagus nerve stimulation and pulse electromagnetic field treatment device newly stimulates vagus nerves with the feedback stimulation signal.

The telemedicine system according to one embodiment may further include a medical staff terminal for outputting information including at least one of the measured biosignal and the regenerated stimulation signal, and the regenerated stimulation signal may be updated based on electroceutical prescription information generated according to the information output from the medical staff terminal.

In accordance with another aspect of the present invention, provided is a personalized vagus nerve stimulation and pulse electromagnetic field treatment device including a stimulator for generating, based on a stimulation signal, at least one of electrical stimulation that stimulates vagus nerves in a form of cranial electrotherapy stimulation (CES) at two or more stimulation sites located on an auricle and an earlobe, respectively, electrical stimulation that stimulates vagus nerves in a form of transcutaneous electrical nerve stimulation (TENS) at two or more stimulation sites located in bilateral carotid arteries of a neck, and a magnetic field that stimulates vagus nerves in a form of pulsed electromagnetic field (PEMF) at stimulation sites located around a brain from a heart; a biosignal monitor for measuring a biosignal that responds to stimulation applied to the vagus nerve and outputting monitoring information including the stimulation signal and the biosignal through an artificial intelligence encoder; and a communicator for transmitting the output monitoring information to a mobile terminal or a server using short-range wireless communication, wherein the stimulator receives a regenerated stimulation signal fed back from the mobile terminal or the server based on a stimulation control model and regenerates electrical stimulation or a magnetic field.

The stimulation control model according to one embodiment may determine whether interaction between a heart and a brain or an autonomic nervous system is abnormal based on variability of a time interval between adjacent heartbeats using heart rate variability (HRV) measured from the biosignal, or may determine whether the autonomic nervous system is abnormal by determining a degree of maintaining blood pressure homeostasis using baroreflex sensitivity (BRS) measured from the biosignal, and regenerate the stimulation signal in real time.

The biosignal monitor according to one embodiment may monitor a brain response by electroencephalogram (EEG) as the biosignal, and may encode and output frontal lobe activation information according to the brain response through an artificial intelligence encoder.

The biosignal monitor according to one embodiment may monitor a nerve response by photoplethysmography (PPG) measured from at least one of an ear, a neck, and a wrist as the biosignal, and may encode and output autonomic nerve information according to the nerve response through an artificial intelligence encoder.

The biosignal monitor according to one embodiment may monitor a body response by physical activity measurement (Actigraph) measured from at least one of an ear, a neck, and a wrist as the biosignal, and may encode and output movement information according to the body response through an artificial intelligence encoder.

The stimulator according to one embodiment may generate electrical stimulation at an intensity of 0 to 20 mA, a frequency band of 0 to 1,000 Hz, and a pulse width of 0 to 1,000 μS or a magnetic field at a frequency band of 0 to 1,000 Hz and a pulse width of 0 to 1,000 μS.

The mobile terminal according to one embodiment may transmit the output monitoring information to a cloud server, the cloud server may extract the stimulation signal and a biosignal that responds according to the stimulation signal from the transmitted monitoring information, provide the extracted stimulation signal and biosignal as inputs of a pre-stored artificial intelligence machine learning algorithm-based stimulation control model, regenerate the biosignal as an output of the stimulation control model into a stimulation signal to be regulated for balance between sympathetic and parasympathetic nerves, and feedback the regenerated stimulation signal to the communicator, and the stimulator may newly generate electrical stimulation or a magnetic field as the feedback stimulation signal.

The mobile terminal according to one embodiment may extract the stimulation signal and a biosignal that responds according to the stimulation signal from the output monitoring information, provide the extracted stimulation signal and biosignal as inputs of a pre-stored artificial intelligence machine learning algorithm-based stimulation control model, regenerate the biosignal as an output of the stimulation control model into a stimulation signal to be regulated for balance between sympathetic and parasympathetic nerves, and feedback the regenerated stimulation signal to the communicator, and the stimulator may newly generate electrical stimulation or a magnetic field as the feedback stimulation signal.

The mobile terminal according to one embodiment may download or periodically update the stimulation control model from the cloud server.

In accordance with still another aspect of the present invention, provided is a server including a monitoring information collector for collecting monitoring information including a biosignal measured when a stimulation signal is generated from a personalized vagus nerve stimulation and pulse electromagnetic field treatment device, and at least one of stimulation of vagus nerves in a form of cranial electrotherapy stimulation (CES) at two or more stimulation sites located on an auricle and an earlobe, respectively, stimulation of vagus nerves in a form of transcutaneous electrical nerve stimulation (TENS) at two or more stimulation sites located in bilateral carotid arteries of a neck, and a magnetic field that stimulates vagus nerves in a form of pulsed electromagnetic field (PEMF) at stimulation sites located around a brain from a heart is generated; a signal extractor for extracting the stimulation signal and a biosignal corresponding to the stimulation signal from the collected monitoring information; an artificial intelligence processor for providing the extracted stimulation signal and biosignal as inputs of a pre-stored artificial intelligence machine learning algorithm-based stimulation control model, and regenerating the biosignal as an output of the stimulation control model into a stimulation signal to be regulated for balance between sympathetic and parasympathetic nerves; and a communicator for performing control to feed back the regenerated stimulation signal to the personalized vagus nerve stimulation and pulse electromagnetic field treatment device.

The artificial intelligence processor according to one embodiment may determine whether interaction between a heart and a brain or an autonomic nervous system is abnormal based on variability of a time interval between adjacent heartbeats using heart rate variability (HRV) measured from the biosignal, or may determine whether the autonomic nervous system is abnormal by determining a degree of maintaining blood pressure homeostasis using baroreflex sensitivity (BRS) measured from the biosignal, and regenerate the stimulation signal in real time.

Among information included in the biosignal, as a result of monitoring a brain response by electroencephalogram (EEG), the artificial intelligence processor according to one embodiment may provide frontal lobe activation information according to the brain response as an input of the artificial intelligence machine learning algorithm-based stimulation control model.

Among information included in the biosignal, as a result of monitoring a nerve response by photoplethysmography (PPG) measured from at least one of an ear, a neck, and a wrist, the artificial intelligence processor according to one embodiment may provide autonomic nerve information according to the nerve response as an input of the artificial intelligence machine learning algorithm-based stimulation control model.

Among information included in the biosignal, as a result of monitoring a body response by physical activity measurement (Actigraph) measured from at least one of an ear, a neck, and a wrist, the artificial intelligence processor according to one embodiment may provide autonomic nerve information according to the body response as an input of the artificial intelligence machine learning algorithm-based stimulation control model.

In accordance with yet another aspect of the present invention, provided is a method of operating a telemedicine system including a step of generating, based on a stimulation signal, through a personalized vagus nerve stimulation and pulse electromagnetic field treatment device, at least one of electrical stimulation that stimulates vagus nerves in a form of cranial electrotherapy stimulation (CES) at two or more stimulation sites located on an auricle and an earlobe, respectively, electrical stimulation that stimulates vagus nerves in a form of transcutaneous electrical nerve stimulation (TENS) at two or more stimulation sites located in bilateral carotid arteries of a neck, a magnetic field that stimulates vagus nerves in a form of pulsed electromagnetic field (PEMF) at stimulation sites located around a brain from a heart; a step of measuring a biosignal in response to the stimulation; a step of transmitting monitoring information including the measured biosignal to a gateway; a step of extracting, by a cloud server, the stimulation signal and a biosignal that responds according to the stimulation signal from monitoring information transmitted through the gateway; a step of providing the extracted stimulation signal and biosignal as inputs of a pre-stored artificial intelligence machine learning algorithm-based stimulation control model; a step of regenerating the biosignal as an output of the stimulation control model into a stimulation signal to be regulated for balance between sympathetic and parasympathetic nerves; and a step of feeding back the regenerated stimulation signal to the personalized vagus nerve stimulation and pulse electromagnetic field treatment device, wherein the personalized vagus nerve stimulation and pulse electromagnetic field treatment device newly stimulates vagus nerves with the feedback stimulation signal.

The method of operating a telemedicine system according to one embodiment may further include a step of outputting, by a medical staff terminal, information including at least one of the measured biosignals and the regenerated stimulation signals; and a step of updating the regenerated stimulation signal based on electroceutical prescription information generated according to the information output by the medical staff terminal.

Advantageous Effects

According to one embodiment, a personalized medical service capable of managing symptoms anytime, anywhere based on artificial intelligence-based personalized biofeedback through digital therapeutics during daily life can be provided.

According to one embodiment, a telemedicine service delivery system in preparation for the post-corona era can be provided.

According to one embodiment, an autonomic nervous system response can be monitored, subjective processing can be eliminated through artificial intelligence stimulation feedback based on the autonomic nervous system response, and a stimulation recipe optimized for a user can be provided.

According to one embodiment, sleep disturbance, emotional disturbance, and digestive symptoms caused by an imbalance of sympathetic and parasympathetic nerves can be alleviated by inducing release of inhibitory neurotransmitters including GABA, serotonin, and norepinephrine in the central nervous system through stimulation of vagus nerves.

According to one embodiment, diseases or related symptoms caused by an imbalance between sympathetic and parasympathetic nerves can be alleviated.

According to one embodiment, overactivation of sympathetic nerves due to chronic pain/stress and affective disorders can be corrected.

According to one embodiment, the limitations of conventional vagus nerve stimulators provided based on manuals can be overcome through personalized vagus nerve stimulation optimization using an artificial intelligence algorithm.

According to one embodiment, the parasympathetic nervous system can be activated for body and mind relaxation.

According to one embodiment, by enhancing metabolism of fibroblasts, chondrocytes, and osteoblasts through magnetic field stimulation and modulating the effects of hormones and neurotransmitters on the receptors of various cells, low back pain, pelvic pain, neuropathic pain, and neuralgia/myalgia can be alleviated, and the treatment effect of fractures can be increased.

DESCRIPTION OF DRAWINGS

FIGS. 2A to 2C are diagrams for explaining the relationship between a personalized vagus nerve stimulation and pulse electromagnetic field treatment device according to one embodiment and nerves being stimulated.

FIGS. 9-11 are flowcharts for explaining a method of operating a personalized vagus nerve stimulation and pulse electromagnetic field treatment device according to embodiments.

BEST MODE

Figure 1:
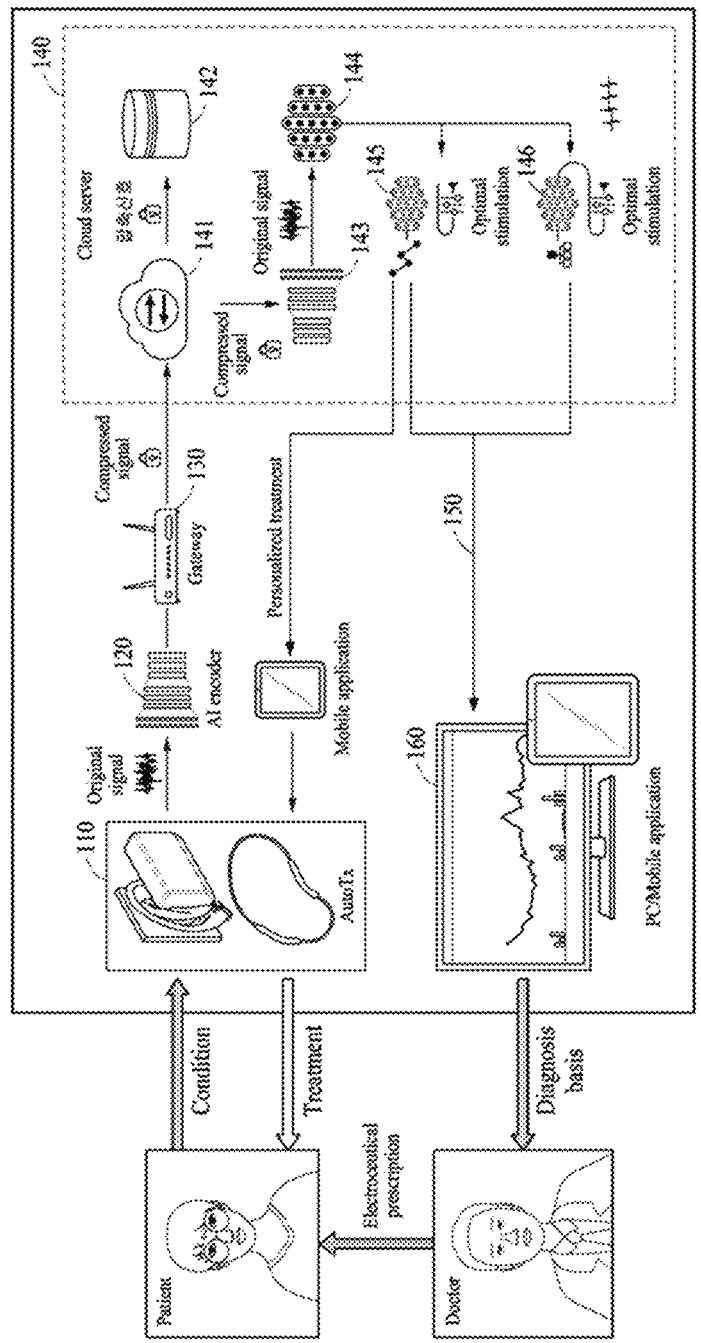
FIG. 1 is a diagram for explaining a telemedicine system using a personalized vagus nerve stimulation and pulse electromagnetic field treatment device according to one embodiment.

Specific structural and functional descriptions of embodiments according to the concept of the present invention disclosed herein are merely illustrative for the purpose of explaining the embodiments according to the concept of the present invention. Furthermore, the embodiments according to the concept of the present invention can be implemented in various forms and the present invention is not limited to the embodiments described herein.

The embodiments according to the concept of the present invention may be implemented in various forms as various modifications may be made. The embodiments will be described in detail herein with reference to the drawings. However, it should be understood that the present invention is not limited to the embodiments according to the concept of the present invention, but includes changes, equivalents, or alternatives falling within the spirit and scope of the present invention.

The terms such as "first" and "second" are used herein merely to describe a variety of constituent elements, but the constituent elements are not limited by the terms. The terms are used only for the purpose of distinguishing one constituent element from another constituent element. For example, a first element may be termed a second element and a second element may be termed a first element without departing from the teachings of the present invention.

It should be understood that when an element is referred to as being "connected to" or "coupled to" another element, the element may be directly connected or coupled to the other element or intervening elements may be present. In contrast, when an element is referred to as being "directly connected to" or "directly coupled to" another element, there are no intervening elements present. Other words used to describe the relationship between elements or layers should be interpreted in a like fashion (e.g., "between," versus "directly between," "adjacent," versus "directly adjacent," etc.).

The terms used In the present specification are used to explain a specific exemplary embodiment and not to limit the present inventive concept. Thus, the expression of singularity in the present specification includes the expression of plurality unless clearly specified otherwise in context. Also, terms such as "include" or "comprise" should be construed as denoting that a certain characteristic, number, step, operation, constituent element, component or a combination thereof exists and not as excluding the existence of or a possibility of an addition of one or more other characteristics, numbers, steps, operations, constituent elements, components or combinations thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, preferred embodiments of the present invention will be described in detail with reference to the accompanying drawings. However, the scope of the present invention is not limited by these embodiments. Like reference numerals in the drawings denote like elements.

FIG. 1 is a diagram for explaining a telemedicine system 100 using a personalized vagus nerve stimulation and pulse electromagnetic field treatment device according to one embodiment.

The telemedicine system 100 according to one embodiment may include a gateway 130 and a cloud server 140.

For example, the gateway 130 may transmit monitoring information including a stimulation signal and a biosignal corresponding to the stimulation signal to a cloud.

The cloud server 140 may extract the stimulation signal and the biosignal from the transmitted monitoring information, and may provide the extracted stimulation signal and biosignal as inputs of a pre-stored artificial intelligence machine learning algorithm-based stimulation control model. In addition, the cloud server 140 may regenerate the biosignal as an output of the stimulation control model into a stimulation signal to be regulated for the balance between sympathetic and parasympathetic nerves, and may feed back the regenerated stimulation signal to the personalized vagus nerve stimulation and pulse electromagnetic field treatment device.

In addition, the monitoring information may include a biosignal measured when vagus nerves are stimulated in the form of electromagnetism at stimulation sites based on a stimulation signal generated from a personalized vagus nerve stimulation and pulse electromagnetic field treatment device 110. In addition, the personalized vagus nerve stimulation and pulse electromagnetic field treatment device may newly stimulate vagus nerves with a feedback stimulation signal.

More specifically, the condition of a patient may be collected through the personalized vagus nerve stimulation and pulse electromagnetic field treatment device 110. In addition, stimulation to improve the condition of a patient by controlling the balance between sympathetic and parasympathetic nerves may also be generated through the personalized vagus nerve stimulation and pulse electromagnetic field treatment device 110.

Types of stimulation generated by the personalized vagus nerve stimulation and pulse electromagnetic field treatment device 110 include vagus nerve stimulation and ASMR.

That is, the serotonin pathway is stimulated through vagus nerve stimulation, and the oxytocin pathway is stimulated through ASMR stimulation to relieve symptoms. The detailed pathway is as follows.

First, referring to the serotonin pathway, the personalized vagus nerve stimulation and pulse electromagnetic field treatment device 110 may stimulate the vagus nerve pathway in the ear and neck, and the vagus nerve stimulation may stimulate the locus coeruleus (LC) via NTS. In addition, LC may stimulate the dorsal raphe nucleus (DRN) by stimulating norepinephrine (NE) secretion, which may stimulate serotonin (5-HT) secretion. An increase in serotonin (5-HT) secretion leads to an increase in melatonin, and sleep disturbance caused by lack of melatonin may be treated.

In addition, the personalized vagus nerve stimulation and pulse electromagnetic field treatment device 110 may autonomous sensory meridian response (ASMR) content.

Referring to the oxytocin pathway, according to the fMRI study conducted to evaluate the effectiveness of ASMR, ASMR activates the medical prefrontal cortex, which may lead to an increase in oxytocin and cause a relaxation response. This mechanism may be used.

According to one embodiment, the personalized vagus nerve stimulation and pulse electromagnetic field treatment device 110 may generate electrical stimulation or a magnetic field based on a stimulation signal, may measure a biosignal in response to the generated electrical stimulation or magnetic field, and may output monitoring information including the stimulation signal and the biosignal through an artificial intelligence encoder 120.

In addition, the personalized vagus nerve stimulation and pulse electromagnetic field treatment device 110 may generate a magnetic field based on a stimulation signal, may measure a biosignal in response to the generated magnetic field, and may output monitoring information including a stimulation signal and the biosignal through an artificial intelligence encoder.

As a specific example of the electrical stimulation, the personalized vagus nerve stimulation and pulse electromagnetic field treatment device 110 may generate electrical stimulation that stimulates vagus nerves in the form of cranial electrotherapy stimulation (CES) at two or more stimulation sites located on an auricle and an earlobe, respectively.

As another example of the electrical stimulation, the personalized vagus nerve stimulation and pulse electromagnetic field treatment device 110 may generate electrical stimulation that stimulates vagus nerves in the form of transcutaneous electrical nerve stimulation (TENS) at two or more stimulation sites located in bilateral carotid arteries of the neck.

As an example of the magnetic field, the personalized vagus nerve stimulation and pulse electromagnetic field treatment device 110 may generate a magnetic field from a coil in the form of a necklace that stimulates vagus nerves in the form of pulsed electromagnetic field (PEMF) at stimulation sites located around the brain from the heart.

The monitoring information output through the artificial intelligence encoder 120 may be transmitted to the cloud server 140 in the form of a compressed signal through the gateway 130.

Specifically, a cloud 141 may maintain a database 142 accessible through a cloud-type communication network.

In the database 142, information about optimal stimulation signals compared to previously measured biosignals of various types may be recorded.

In addition, the monitoring information transmitted to the cloud 141 is decoded through an artificial intelligence decoder 143, and then an artifact removal process may be performed in a signal quality management artificial intelligence 144 in the form of an original signal.

In addition, the artifact-removed monitoring information may be provided as an input of an artificial intelligence machine learning algorithm-based stimulation control model 145 for optimal stimulation. In addition, the artifact-removed monitoring information having improved quality may be provided as an input of another stimulation control model 146 with reduced risk.

The biosignal as an output of the stimulation control model may be regenerated into a stimulation signal to be regulated for the balance between sympathetic and parasympathetic nerves.

The mobile terminal may display biosignals measured by the personalized vagus nerve stimulation and pulse electromagnetic field treatment device 110 or monitoring information processed through the cloud server 140 to a patient through an output means such as a display.

In the embodiment of FIG. 1, the present invention is described as the stimulation control model 145 or the stimulation control model 146 being driven in the cloud server 140. However, the stimulation control model 145 and the stimulation control model 146 or either one may be driven in a mobile terminal in the form of a mobile application.

In addition, after confirming output information 150 from the stimulation control model 145 or the stimulation control model 146 through an output means 160, a doctor may give an electroceutical prescription to a patient. The electroceutical prescription may be interpreted as various inputs capable of changing electrical stimulation or a magnetic field generated by the personalized vagus nerve stimulation and pulse electromagnetic field treatment device 110.

For example, the electroceutical prescription may be interpreted as a weight that may differently adjust the amplitude of electrical stimulation or a magnetic field in relation to a stimulation signal regenerated by the stimulation control model 145.

According to the present invention, personalized medicine that may manage symptoms anytime, anywhere based on artificial intelligence-based personalized biofeedback through digital therapeutics during daily life is possible. In addition, a telemedicine service delivery system in preparation for the post-corona era may be provided.

A photoplethysmogram sensor capable of measuring pulse waves in the earlobe, a photoplethysmogram sensor capable of measuring pulse waves in carotid arteries, a wrist-type photoplethysmogram sensor capable of measuring pulse waves from the wrist, a dry electroencephalography sensor located at the frontal lobe close to the forehead, G/W for patient data collection by ward, cloud server linkage technology, environment setting, technology related to hospital, ward, and bed number, patient-specific data collection and storage technology, server linkage technology using MQTT, SockedO, etc., battery low event transmission technology, process monitoring and automatic failover, device linkage technology, device node automatic search, registration, and connection technology, BLE communication interface technology, device data (ECG, IMU) collection technology, device battery level check technology, and the like may be applied to the personalized vagus nerve stimulation and pulse electromagnetic field treatment device 110.

Figure 2A:
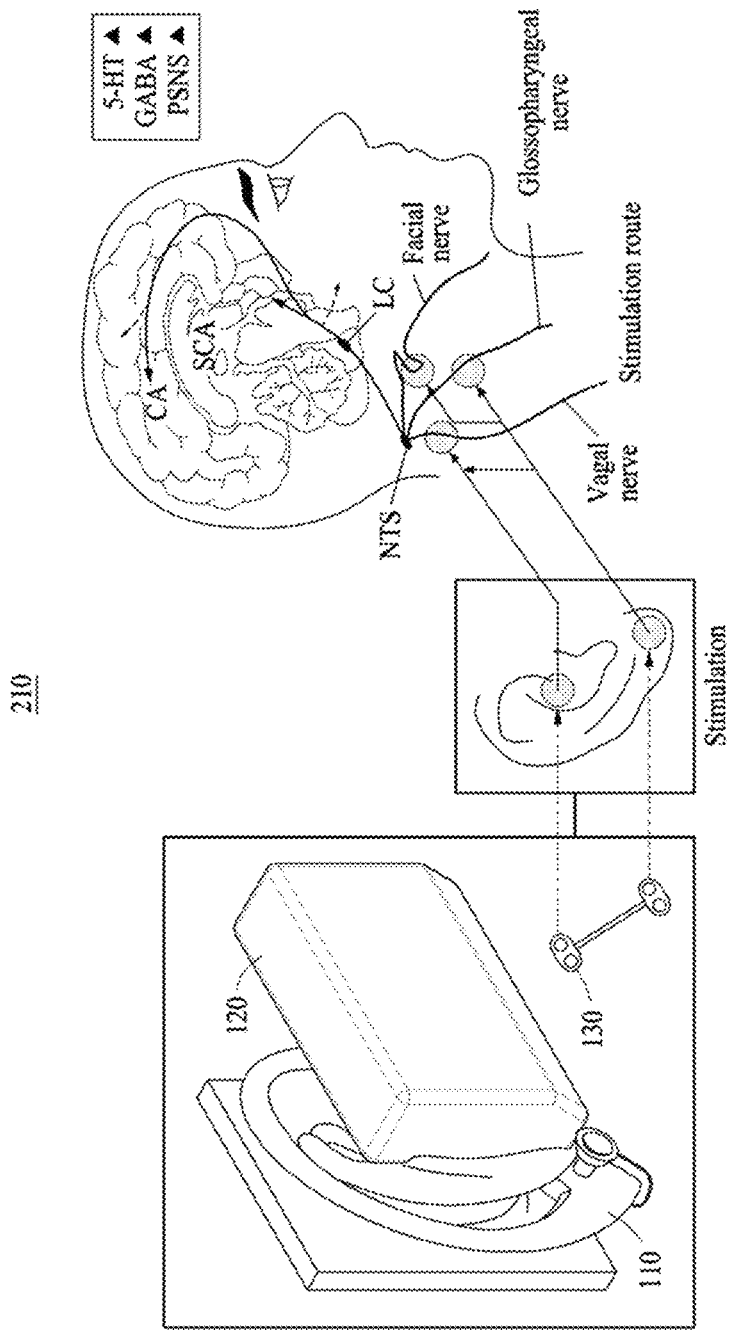

FIGS. 2A to 2C are diagrams for explaining the relationship between a personalized vagus nerve stimulation and pulse electromagnetic field treatment device according to one embodiment and nerves being stimulated.

A personalized vagus nerve stimulation and pulse electromagnetic field treatment device 210 according to one embodiment may supply stimulation in the form of electrical stimulation or a magnetic field to a user, and may provide customized stimulation suitable for the user to balance between sympathetic and parasympathetic nerves.

Stimulation signals may be regenerated based on hypotheses proven in various existing papers.

Through a stimulation presence/absence experiment, which is an experiment for observing changes in the user's state before/after stimulation, it is possible to check whether a change in the user's state occurs before and after stimulation is given through vagus nerve stimulation.

In addition, as an experiment for observing a change in the user's state when a stimulus is actually given and when a false stimulus is given, it may be confirmed whether there is a change in the user's state even when a false stimulus is given through a false stimulus experiment.

In addition, as an experiment for observing a change in the user's state after showing a fear image and when a stimulus is applied after the anxiety state, it may be confirmed whether the user's state is stabilized through vagus nerve stimulation when the user is in an anxiety state through the fear experiment.

For example, referring to Yu, Zhang et al. 2009, it can be seen that a power decreases when sympathetic nerve activation occurs due to reasons such as stress. Accordingly, when activation of parasympathetic nerves induces inactivation of sympathetic nerves, a power is expected to increase and become a calm state. In fact, when vagus nerves are stimulated using electromagnetic stimulation, it can be confirmed that power increases at all frequencies. In particular, increase in a power may be interpreted as the result that activation of parasympathetic nerves may induce inactivation of sympathetic nerves.

In addition, as a fear experiment, in the δ band, power continuously increases after stimulation. In the e, a, and a bands, power initially increases 10 minutes after stimulation is given, but power decreases after stimulation is stopped.

In the case of a and a power, it can be seen that when watching a horror video, the power decreases and then increases after stimulation. In Herrmann, Struber et al. 2016, in the case of a power, it is explained that power inhibition occurs when a person cannot concentrate on something.

Accordingly, it may be thought that alpha power decreased because a person could not concentrate on a scary video, and alpha power increased when the video ended later.

Howells, according to Stein et al. 2010, it is reported that beta power is affected by attention.

That is, it can be seen that the a and a bands are related to attention, and it can be interpreted that attention decreased when fear was felt, and anxiety was also felt. When the vagus nerve is stimulated through electromagnetic stimulation, this phenomenon may cause a change to a relaxed state.

A personalized vagus nerve stimulation and pulse electromagnetic field treatment device 100 according to one embodiment may stimulate vagus nerves around the ear using cranial electrotherapy stimulation (CES).

Specifically, the personalized vagus nerve stimulation and pulse electromagnetic field treatment device 100 according to one embodiment may stimulate vagus nerves distributed in the concha and earlobe based on transcutaneous electrical nerve stimulation (TENS) in the vicinity of the ear.

The personalized vagus nerve stimulation and pulse electromagnetic field treatment device 210 according to one embodiment may include a hanger 211 for fixing to the ear and a main body 222 that is physically fixed to the hanger 2110 and stimulates vagus nerves distributed in the concha and the earlobe.

As shown by reference numeral 223, in the main body 222, electrical stimulation that stimulates vagus nerves in a form of cranial electrotherapy stimulation (CES) at two or more stimulation sites located on an auricle and an earlobe, respectively, may be generated through stimulation contact points. Electrical stimulation may be generated according to an electrical signal, and the electrical signal may be adjusted in real time according to a user's biological signal.

Electrical stimulation by stimulation contact points 223 may stimulate vagus nerves distributed in the concha and the earlobe based on transcutaneous electrical nerve stimulation.

In FIG. 2A, PSNS represents a parasympathetic nervous system, NTS represents the nucleus tractus solitaries, LC represents the locus coeruleus, SCA represents the subcortical area, and CA represents the cortical area.

In addition, the stimulation contact points 223 may generate electrical stimulation that stimulates vagus nerves in the form of CES based on a stimulation signal, and may generate electrical stimulation at an intensity of 0 to 20 mA, a frequency band of 0 to 1,000 Hz, and a pulse width of 0 to 1,000 μS.

The personalized vagus nerve stimulation and pulse electromagnetic field treatment device 100 according to one embodiment may monitor a biosignal by the electrical stimulation.

In addition, the personalized vagus nerve stimulation and pulse electromagnetic field treatment device 210 according to one embodiment may transmit the monitored biosignal to a mobile terminal or a cloud server, may receive a new stimulation signal calculated based on the biosignal, and may newly stimulate in the form of CES at two or more stimulation sites located on the auricle and the earlobe, respectively.

At this time, the mobile terminal or the cloud server may generate a personalized stimulation signal using an artificial intelligence machine learning algorithm-based stimulation control model.

In addition, the mobile terminal may download or periodically update the stimulation control model from the cloud server.

Specifically, the artificial intelligence machine learning algorithm-based stimulation control model may receive a stimulation signal and a biosignal in response to the stimulation signal, and may regenerate the biosignal into a stimulation signal to be regulated for the balance between sympathetic and parasympathetic nerves.

For example, the mobile terminal (or mobile application) may collect HRV and BRS, which are clinical parameters capable of identifying a user's state, from the personalized vagus nerve stimulation and pulse electromagnetic field treatment device, and may transmit signals and the clinical parameters to a cloud server.

Thus, the cloud server may balance the target sympathetic and parasympathetic nerves by using signals and clinical parameters transmitted from the mobile terminal (or mobile application) as input features of the artificial intelligence-based model.

The stimulation control model according to one embodiment may determine whether interaction between the heart and the brain or an autonomic nervous system is abnormal based on the variability of a time interval between adjacent heartbeats using heart rate variability (HRV) measured from a biosignal.

The stimulation control model may determine whether an autonomic nervous system is abnormal by determining a degree of maintaining blood pressure homeostasis using baroreflex sensitivity (BRS) measured from a biosignal, and regenerate the stimulation signal in real time.

The personalized vagus nerve stimulation and pulse electromagnetic field treatment device 210 according to one embodiment may monitor various biosignals as feedback on electrical stimulation.

For example, the personalized vagus nerve stimulation and pulse electromagnetic field treatment device 210 according to one embodiment may monitor a brain response by an electroencephalogram (EEG), and may encode and output frontal lobe activation information according to the brain response through an artificial intelligence encoder.

The personalized vagus nerve stimulation and pulse electromagnetic field treatment device 210 according to one embodiment may receive EEG measured by a separate device and monitor a brain response by the EEG, or may monitor a brain response by EEG by measuring the EEG through an integrated module.

As another example, the personalized vagus nerve stimulation and pulse electromagnetic field treatment device 210 according to one embodiment may monitor a nerve response by photoplethysmography (PPG) measured from at least one of the ear, the neck, and the wrist, and may encode and output autonomic nerve information according to the nerve response through an artificial intelligence encoder.

As another example, the personalized vagus nerve stimulation and pulse electromagnetic field treatment device 210 according to one embodiment may monitor a body response by physical activity measurement (Actigraph) measured from at least one of the ear, the neck, and the wrist, and may encode and output movement information according to the body response through an artificial intelligence encoder.

A personalized vagus nerve stimulation and pulse electromagnetic field treatment device 220 according to an embodiment of FIG. 2B may stimulate vagus nerves using transcutaneous electrical nerve stimulation (TENS) at two or more stimulation sites located in bilateral carotid arteries of the neck.

Specifically, the personalized vagus nerve stimulation and pulse electromagnetic field treatment device 220 according to one embodiment may vagus nerves distributed in bilateral carotid arteries based on transcutaneous electrical nerve stimulation (TENS) in the vicinity of the ear.

The personalized vagus nerve stimulation and pulse electromagnetic field treatment device 220 according to one embodiment be divided into the main body 222 capable of stimulating vagus nerves distributed in bilateral carotid arteries.

In the main body 222, electrical stimulation that stimulates vagus nerves in the form of transcutaneous electrical nerve stimulation (TENS) at two or more stimulation sites located in bilateral carotid arteries of the neck may be generated. The electrical stimulation may be generated according to a stimulation signal, and the stimulation signal may be adjusted in real time according to a user's biosignal.

Electrical stimulation by stimulation contact points may stimulate vagus nerves distributed in bilateral carotid arteries based on transcutaneous electrical nerve stimulation.

In FIG. 2B, PSNS represents a parasympathetic nervous system, NTS represents the nucleus tractus solitaries, LC represents the locus coeruleus, SCA represents the subcortical area, and CA represents the cortical area.

In addition, the stimulation contact points may generate electrical stimulation that stimulates vagus nerves in the form of transcutaneous electrical nerve stimulation (TENS) based on a stimulation signal, and may generate the electrical stimulation at an intensity of 0 to 20 mA, a frequency band of 0 to 1,000 Hz, and a pulse width of 0 to 1,000 μS.

The personalized vagus nerve stimulation and pulse electromagnetic field treatment device 220 according to one embodiment may monitor a biosignal by the electrical stimulation.

In addition, the personalized vagus nerve stimulation and pulse electromagnetic field treatment device 220 according to one embodiment may transmit the monitored biosignal to a mobile terminal or a cloud server, may receive a new stimulation signal calculated based on the biosignal, and may newly stimulate in the form of TENS in a heart stimulation pathway of vagus nerves among two or more stimulation sites located at bilateral carotid arteries of the neck.

As shown in an embodiment of FIG. 2B, the personalized vagus nerve stimulation and pulse electromagnetic field treatment device 220 may be implemented in the form of a necklace 221, and electrical stimulation may be generated by a stimulation signal through a pair of electric electrodes located at the ends of a stimulator 222.

The electrical stimulation by the stimulation signal may be generated at an intensity of 0 to 20 mA, a frequency band of 0 to 1,000 Hz, and a pulse width of 0 to 1,000 μS.

The personalized vagus nerve stimulation and pulse electromagnetic field treatment device 220 in the necklace form 221 may provide a neurofeedback system for stabilizing an autonomic nervous system based on artificial intelligence through transcutaneous electrical nerve stimulation of vagus nerves around bilateral carotid arteries. Thus, parasympathetic nerve activation may be induced through TENS stimulation of vagus nerves, which are distributed around bilateral carotid arteries and extend from the heart, lungs, and internal organs.

Referring to FIG. 2C, a personalized vagus nerve stimulation and pulse electromagnetic field treatment device 230 according to one embodiment may stimulate vagus nerves in the form of pulsed electromagnetic field (PEMF) at stimulation sites located around the brain.

Specifically, the personalized vagus nerve stimulation and pulse electromagnetic field treatment device 230 according to one embodiment may stimulate vagus nerves distributed in bilateral carotid arteries.

The personalized vagus nerve stimulation and pulse electromagnetic field treatment device 230 according to one embodiment may be divided into stimulators 232 and 233 capable of stimulating vagus nerves distributed in bilateral carotid arteries.

The stimulators 232 and 233 may include a coil or a solenoid capable of generating a magnetic field, and may stimulate vagus nerves in the form of pulsed electromagnetic field (PEMF) at stimulation sites located around the brain by a stimulation signal. The stimulation signal for generating the magnetic field may be regulated in real time according to a user's biosignal.

In FIG. 2C, PSNS represents a parasympathetic nervous system, NTS represents the nucleus tractus solitaries, LC represents the locus coeruleus, SCA represents the subcortical area, and CA represents the cortical area.

In addition, the personalized vagus nerve stimulation and pulse electromagnetic field treatment device 230 according to one embodiment may transmit the monitored biosignal to a mobile terminal or a cloud server, may receive a new stimulation signal calculated based on the biosignal, and may stimulate vagus nerves in the form of pulsed electromagnetic field (PEMF) at stimulation sites located around the brain.

As shown in an embodiment of FIG. 2C, a personalized vagus nerve stimulation and pulse electromagnetic field treatment device 230 may be implemented in the form of a necklace 231. Vagus nerves distributed around the heart and the brain may be stimulated using a pulsed electromagnetic field (PEMF) through magnetic fields generated by the stimulators 232 and 233.

Hereinafter, in FIG. 3, operation of specific components that monitor a biosignal according to electrical stimulation or a magnetic field by a stimulation signal and generate a new stimulation signal fed back according to the monitored biosignal will be described.

Figure 3:
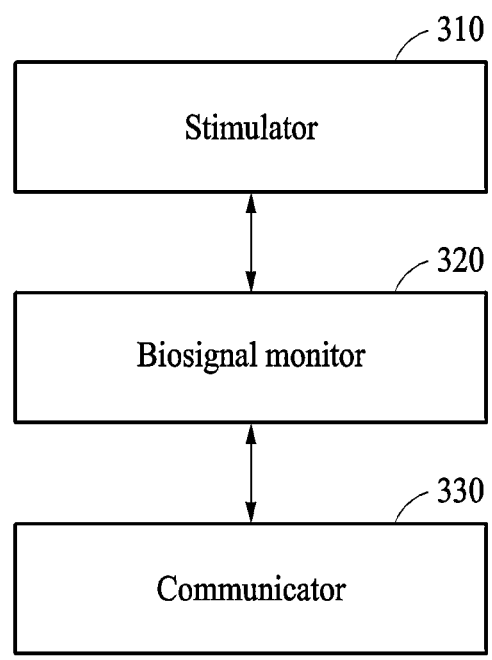
FIG. 3 is a diagram showing the components of a personalized vagus nerve stimulation and pulse electromagnetic field treatment device according to one embodiment.

FIG. 3 is a diagram for explaining the components of a personalized vagus nerve stimulation and pulse electromagnetic field treatment device 300 according to one embodiment.

The personalized vagus nerve stimulation and pulse electromagnetic field treatment device 300 may monitor an autonomic nervous system response, may eliminate subjective processing through artificial intelligence stimulation feedback based on the autonomic nervous system response, and may provide a stimulation recipe optimized for a user.

For example, in the case of patients with anxiety disorders, sudden panic attack may be considered.

In this case, the personalized vagus nerve stimulation and pulse electromagnetic field treatment device 300 may obtain a biosignal collected from a user. Based on the biosignal, a cloud server may calculate clinical parameters by using an artificial intelligence-based model, and may determine a threshold-based sympathetic and parasympathetic nerve activation level. In addition, by targeting a normalization section of sympathetic and parasympathetic nerves for normalization of the autonomic nervous system, stimulation patterns of intensity, frequency, and width of stimulation that may most effectively stimulate parasympathetic nerves may be derived, and a stimulation signal may be regenerated and fed back to the personalized vagus nerve stimulation and pulse electromagnetic field treatment device 300.

In addition, by using the present invention, release of inhibitory neurotransmitters including GABA, serotonin, and norepinephrine within the central nervous system may be induced, and sleep disturbance, emotional disturbance, and digestive symptoms caused by an imbalance of sympathetic and parasympathetic nerves may be alleviated.

The personalized vagus nerve stimulation and pulse electromagnetic field treatment device 300 may include a stimulator 310, a biosignal monitor 320, and a communicator 330.

First, the stimulator 310 may generate electrical stimulation or a magnetic field for stimulating vagus nerves based on a stimulation signal.

In particular, the stimulator 310 according to one embodiment may generate electrical stimulation or a magnetic field based on a stimulation signal.

In addition, the stimulator 310 may receive the regenerated stimulation signal fed back based on a stimulation control model, and may regenerate electrical stimulation or a magnetic field.

The stimulation control model may be driven in the form of a mobile application in a mobile terminal or in the form of a modeling engine in a cloud server.

In addition, a part of the stimulation control model may be driven in the form of a mobile application in a mobile terminal, and the remaining part thereof may be driven in the form of a modeling engine in a cloud server.

According to one embodiment, the stimulation control model may determine whether interaction between the heart and the brain or an autonomic nervous system is abnormal based on the variability of a time interval between adjacent heartbeats using heart rate variability (HRV) measured from a biosignal.

In addition, the stimulation control model may determine whether an autonomic nervous system is abnormal by determining a degree of maintaining blood pressure homeostasis using baroreflex sensitivity (BRS) measured from a biosignal, and regenerate the stimulation signal in real time.

In the stimulation control model according to one embodiment, abnormality may be determined using both HRV and BRS.

In addition, in the stimulation control model, transfer and reinforcement learning-based algorithms may be implemented. In addition, learning elements in each algorithm may be Action, Reward, Environment, and State.

First, Action corresponds to an element for vagus nerve stimulation through ASMR, TENS, and PEMF, Reward is a response to stimulation, and Reward based on sympathetic or parasympathetic nerve change may be extracted.

In addition, Environment may proceed with learning based on the user's body response to a stimulus. In particular, the body response such as HRV or BRS may be interpreted as a change in a biosignal due to electrical stimulation or a magnetic field.

State corresponds to an Environment information-based user state monitoring function.

Next, the biosignal monitor 320 may measure a biosignal that responds according to a stimulation signal for vagus nerves.

For example, the biosignal monitor 320 may monitor a brain response by electroencephalogram (EEG) as a biosignal that responds to a stimulation signal for vagus nerves. The biosignal monitor 320 may measure frontal lobe activation information according to the brain response.

In addition, the biosignal monitor 320 may monitor a nerve response by photoplethysmography (PPG) measured from at least one of the ear, the neck, and the wrist as a biosignal that responds to a stimulation signal for vagus nerves. The biosignal monitor 320 may measure autonomic nerve information according to the nerve response.

In addition, the biosignal monitor 320 may monitor a body response by physical activity measurement (Actigraph) measured from at least one of the ear, the neck, and the wrist. The biosignal monitor 320 may measure movement information according to the body response.

In addition, the biosignal monitor 320 may output monitoring information including the stimulation signal and the biosignal through an artificial intelligence encoder.

The communicator 330 may transmit output monitoring information to a mobile terminal using short-range wireless communication.

For example, the communicator 330 may transmit output monitoring information to a mobile terminal through a communication method such as Bluetooth or Wi-Fi.

According to one embodiment, the mobile terminal may implement the artificial intelligence machine learning algorithm-based stimulation control model through a mobile application.

In this case, monitoring information transmitted by the communicator 330 may be processed in the mobile terminal.

Specifically, the mobile terminal may extract a stimulation signal and a biosignal in response to the stimulation signal from the output monitoring information.

In addition, the mobile terminal may provide the extracted stimulation signal and biosignal as inputs of a pre-stored artificial intelligence machine learning algorithm-based stimulation control model, and may regenerate the biosignal as an output of the stimulation control model into a stimulation signal to be regulated for the balance between sympathetic and parasympathetic nerves. In addition, the mobile terminal may feed back the regenerated stimulation signal to the communicator 330.

The stimulator 310 may newly generate electrical stimulation or a magnetic field with the feedback stimulation signal.

According to one embodiment, the cloud server may maintain the artificial intelligence machine learning algorithm-based stimulation control model, and may regenerate a stimulation signal.

The mobile terminal performs a function of transmitting monitoring information to the cloud server.

Specifically, a cloud server may extract a stimulation signal and a biosignal in response to the stimulation signal from the transmitted monitoring information.

In addition, the cloud server may provide the extracted stimulation signal and biosignal as inputs of a pre-stored artificial intelligence machine learning algorithm-based stimulation control model, and may regenerate the biosignal as an output of the stimulation control model into a stimulation signal to be regulated for the balance between sympathetic and parasympathetic nerves.

The cloud server may feed back the regenerated stimulation signal to the communicator, and the stimulator 310 may newly generate electrical stimulation or a magnetic field with the feedback stimulation signal.

Figure 4:
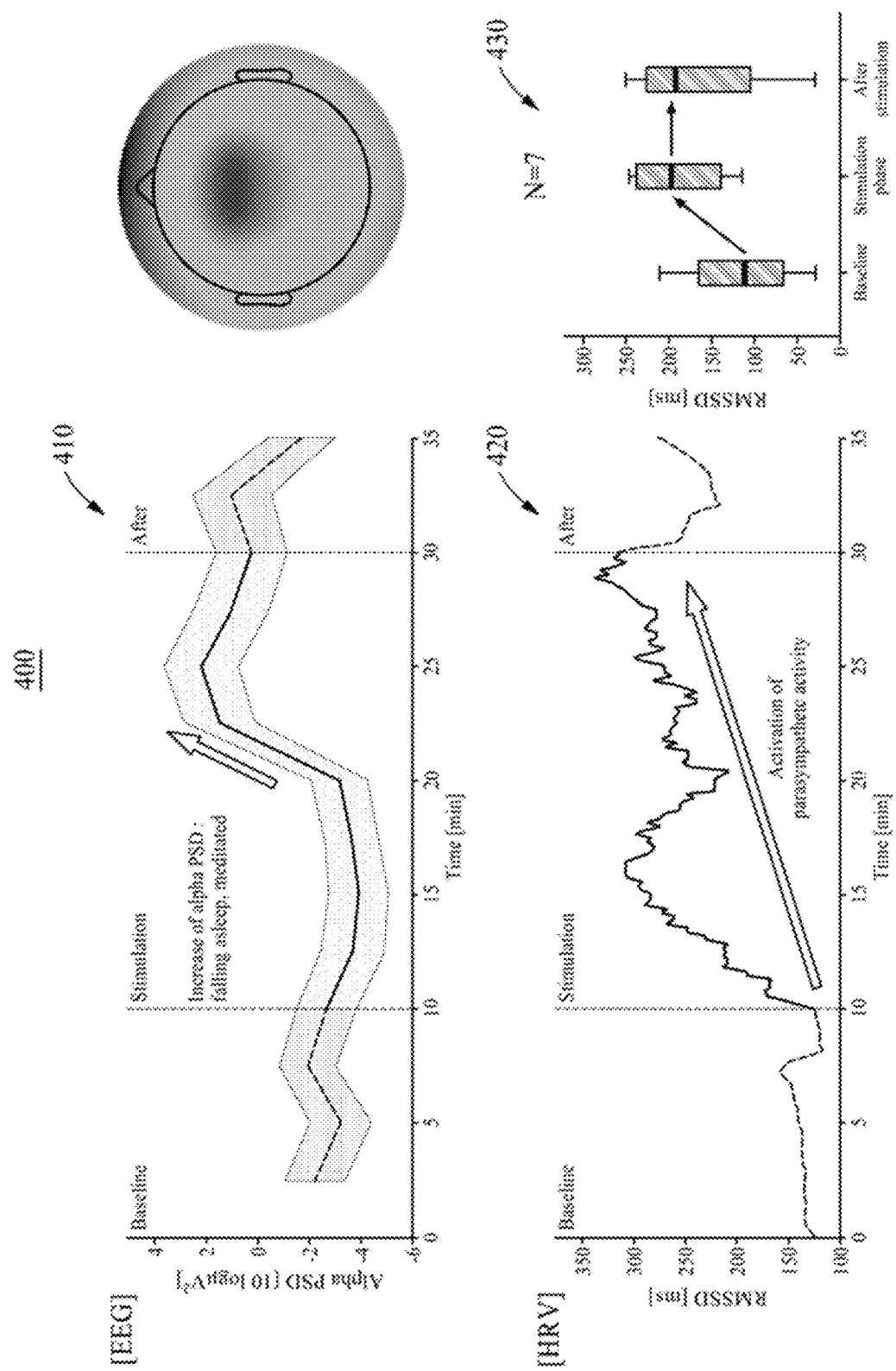
FIG. 4 includes graphs showing alpha waves and activation of parasympathetic nerves while providing stimulation through a personalized vagus nerve stimulation and pulse electromagnetic field treatment device according to one embodiment.

FIG. 4 is a graph 400 showing alpha waves and activation of parasympathetic nerves while providing stimulation through a personalized vagus nerve stimulation and pulse electromagnetic field treatment device according to one embodiment.

The personalized vagus nerve stimulation and pulse electromagnetic field treatment device according to one embodiment may induce brain stimulation through various neural pathways, leading to normalization of the autonomic nervous system.

The personalized vagus nerve stimulation and pulse electromagnetic field treatment device according to one embodiment may monitor a brain response by electroencephalogram (EEG) as a biosignal.

In particular, parasympathetic nerve activity may be induced through stimulation of vagus nerves distributed in the concha and earlobe based on transcutaneous electrical nerve stimulation. For example, the personalized vagus nerve stimulation and pulse electromagnetic field treatment device according to one embodiment may monitor change in the state of the user's autonomic nervous system, and based on the monitoring results, may optimize TEN of vagus nerves of the concha and the earlobe in real time.

The personalized vagus nerve stimulation and pulse electromagnetic field treatment device according to one embodiment may check frontal lobe activation information according to a brain response. As shown in reference numeral 410, when stimulation is applied with an optimal stimulation signal, alpha PSD significantly increases, and activation of alpha waves and parasympathetic nerves may be observed. In addition, as shown in reference numeral 420, activation of alpha waves and parasympathetic nerves may be observed through significant change by RMSSD in a specific section. In addition, as shown in reference numeral 430, RMSSD significantly increases after electrical stimulation or a magnetic field continues from a baseline.

For reference, looking at heart rate variability variables related to parasympathetic nerves, change in an R-R interval in mean RR is used to identify the activity patterns of the sympathetic and parasympathetic nervous systems. As the value increases, a heart rate decreases, and at the same time, the parasympathetic nervous system is activated.

The root mean square of the successive differences (RMSSD) indicates whether the parasympathetic nervous system is well regulated in the heart, and a high value may be interpreted as a healthy state.

The high frequency (HF) band means a high frequency band and is associated with heart rate variability associated with the respiratory cycle. This frequency band is known to exhibit activation of parasympathetic nerves or vagus nerves.

The LF/HF ratio is the ratio of power in the low frequency band to the high frequency band, and decrease in the value means that parasympathetic nerves are activated or activity of sympathetic nerves is inhibited. The mean heart rate (HR) is an average heart rate, and decrease in the value means that the parasympathetic nervous system is activated This phenomenon is caused by a personalized stimulation design algorithm based on reinforcement learning and transfer learning considering various vagus nerve stimulation pathways. By using the source technology of autoencoder customized for biosignals, autonomic nervous system response evaluation and stimulation control may be secured in real time. In addition, unlike existing technologies that simply increase or decrease intensity, real time customized stimulation is possible in that stimulation intensity is adjusted according to the degree of activity of targeted sympathetic/parasympathetic nerves.

In addition, the personalized vagus nerve stimulation and pulse electromagnetic field treatment device may monitor a nerve response by photoplethysmography (PPG) measured from at least one of the ear, the neck, and the wrist as a biosignal, and may encode autonomic nerve information according to the nerve response through an artificial intelligence encoder.

In particular, the personalized vagus nerve stimulation and pulse electromagnetic field treatment device may induce parasympathetic nerve activation through TENS stimulation of vagus nerves that extend from the heart, lungs, or internal organs distributed around bilateral carotid arteries.

That is, the personalized vagus nerve stimulation and pulse electromagnetic field treatment device may monitor change in the state of the user's autonomic nervous system, and based on the monitoring results, may optimize TENS of vagus nerves of bilateral carotid arteries in real time.

In addition, the personalized vagus nerve stimulation and pulse electromagnetic field treatment device may generate a magnetic field from a coil in the form of a necklace that stimulates vagus nerves in the form of pulsed electromagnetic field (PEMF) at stimulation sites located around the brain from the heart, may monitor a biosignal in response to the stimulation, and may encode autonomic nerve information according to the biosignal through an artificial intelligence encoder.

In particular, the personalized vagus nerve stimulation and pulse electromagnetic field treatment device may stimulate vagus nerves distributed around the heart and the brain through magnetic stimulation emitted from a coil or solenoid in the form of a necklace.

Through this, change in the state of the user's autonomic nervous system may be monitored, and the personalized vagus nerve stimulation and pulse electromagnetic field treatment device may implement real time optimization of vagus nerve PEMF based on the monitoring results.

For example, activation of vagus nerves stimulates periaqueductal gray (PAG) via nucleus of solitary tract (NTS), and PAG promotes GABA secretion. Eventually, increased GABA inhibits hippocampus activity, thereby alleviating symptoms of anxiety disorders.

In addition, vagus nerve stimulation may stimulate the locus coeruleus (LC) through NTS. LC stimulates dorsal raphe nucleus (DRN) by stimulating norepinephrine (NE) secretion, which may stimulate serotonin (5-HT) secretion. In addition, an increase in serotonin (5-HT) secretion leads to an increase in melatonin, which may treat sleep disturbance caused by melatonin deficiency.

Figure 5:
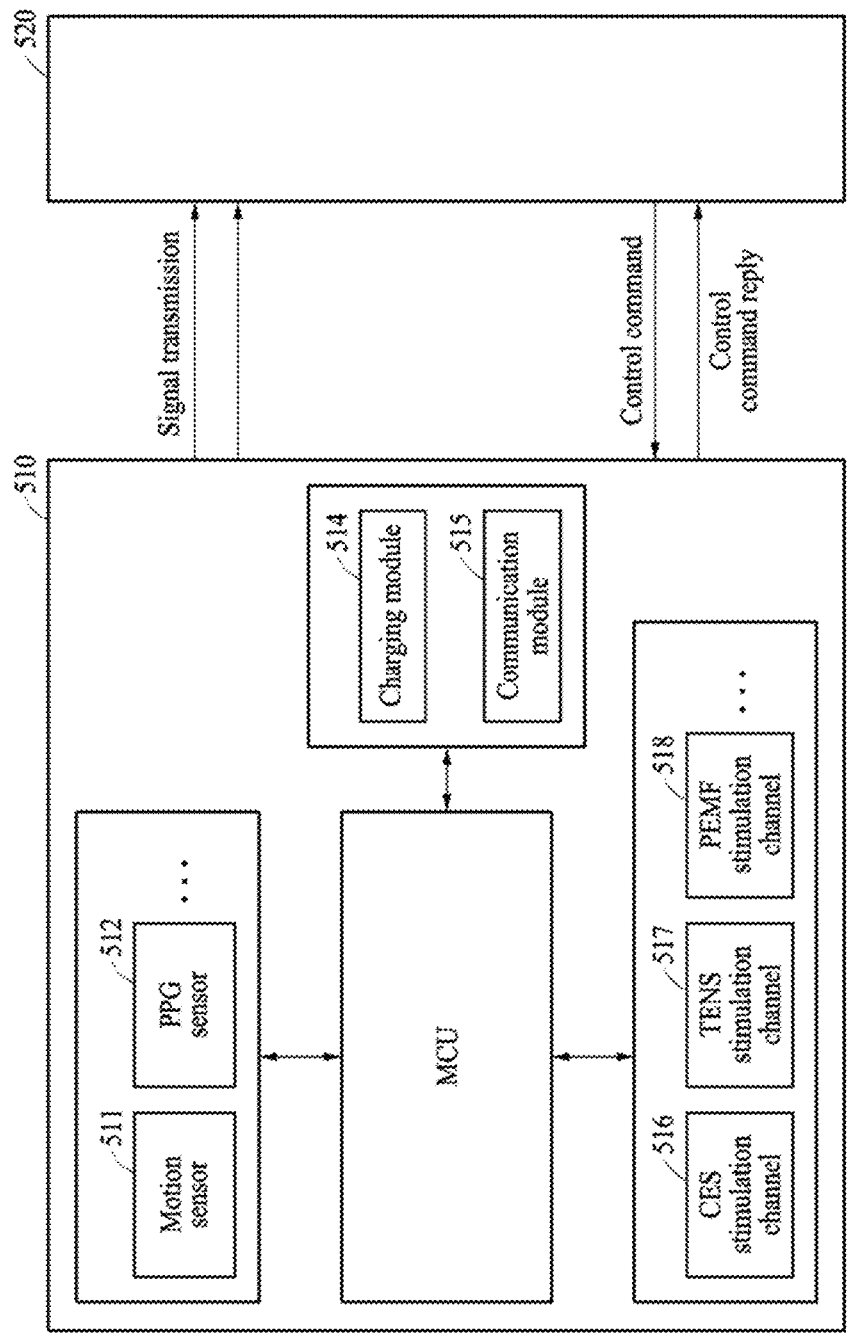
FIG. 5 is a diagram illustrating a specific implementation example of a personalized vagus nerve stimulation and pulse electromagnetic field treatment device and a main event flow.

FIG. 5 a diagram illustrating a specific implementation example of a personalized vagus nerve stimulation and pulse electromagnetic field treatment device 510 and a major event flow.

A biosignal monitor according to one embodiment may monitor a biosignal through at least one sensor. Specifically, the biosignal monitor may be implemented using a motion sensor 511 that senses the user's motion or a PPG sensor 512 that monitors a neural response by photoplethysmography (PPG) measured from at least one of the user's ear, neck, or wrist.

The biosignal may be interpreted as various information measured from a living body as vagus nerves of a part of the body are stimulated with electromagnetism. This variety of information may be measured by various devices, and various sensors other than the motion sensor 511 or the PPG sensor 512 shown in FIG. 5 may be added or replaced.

In addition, a micro control unit (MCU) 513 may be responsible for signal processing along with overall control of each component.

A charging module 514 is a module for supplying DC power to the personalized vagus nerve stimulation and pulse electromagnetic field treatment device 510, and may include a rechargeable battery.

A communicator according to one embodiment may include a communication module 515. The communication module 515 is a module for providing a wired/wireless communication function to the personalized vagus nerve stimulation and pulse electromagnetic field treatment device 510. For example, the communication module 515 provides a short-range wireless communication function using a low-power Bluetooth/Wi-Fi module, or enables wired/wireless data communication by accessing a network.

A stimulator according to one embodiment may include at least one of various stimulation channels for generating electrical stimulation or a magnetic field.

The stimulator according to one embodiment may include at least one stimulation channel of a CES stimulation channel 516, a TENS stimulation channel 517, and a PEMF stimulation channel 518.

Although FIG. 5 shows all of the various stimulation channels, a form including only one stimulation channel may be implemented for the purpose of generating a specific stimulation signal.

For example, the CES stimulation channel 516 may generate electrical stimulation for stimulating vagus nerves in the form of cranial electrotherapy stimulation (CES) at two or more stimulation sites located on the auricle and the earlobe, respectively.

In addition, the TENS stimulation channel 517 may generate electrical stimulation for stimulating vagus nerves distributed in the concha and the earlobe based on transcutaneous electrical nerve stimulation (TENS) in the vicinity of the ear.

In addition, the PEMF stimulation channel 518 may generate a magnetic field that stimulates vagus nerves in the form of pulsed electromagnetic field (PEMF) at stimulation sites located around the brain from the heart.

Reference numeral 520 may be interpreted as an entity for interworking with the personalized vagus nerve stimulation and pulse electromagnetic field treatment device 510 and regenerating a stimulation signal based on a stimulation control model according to monitored biosignal.

According to an embodiment, reference numeral 520 may be interpreted as a remote cloud server or a mobile application of a mobile terminal located in a short distance.

In addition, reference numeral 520 may also be interpreted as an artificial intelligence processing module implemented in the personalized vagus nerve stimulation and pulse electromagnetic field treatment device 510 and one device.

Figure 6:
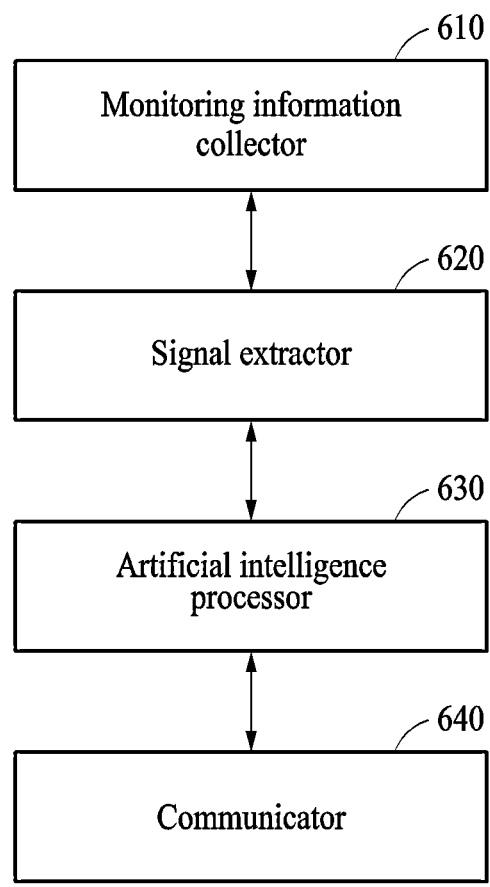
FIG. 6 is a diagram for explaining a cloud server according to one embodiment.

FIG. 6 is a diagram illustrating a cloud server 600 according to one embodiment.

The cloud server 600 according to one embodiment may provide an optimization stimulus to the personalized vagus nerve stimulation and pulse electromagnetic field treatment device.

The cloud server 600 according to one embodiment may include a monitoring information collector 610, a signal extractor 620, an artificial intelligence processor 630, and a communicator 640.

First, the monitoring information collector 610 may collect monitoring information including a biosignal.

The biosignal may be interpreted as information measured when the personalized vagus nerve stimulation and pulse electromagnetic field treatment device generates a stimulation signal to stimulate vagus nerves in the form of cranial electrotherapy stimulation (CES) at two or more stimulation sites located on the auricle and the earlobe, respectively.

In addition, the monitoring information collector 610 may collect monitoring information including a biosignal measured when the personalized vagus nerve stimulation and pulse electromagnetic field treatment device generates at least one of a stimulation signal that stimulates vagus nerves in the form of transcutaneous electrical nerve stimulation (TENS) at two or more stimulation sites located in bilateral carotid arteries of the neck or a magnetic field that stimulates vagus nerves in the form of pulsed electromagnetic field (PEMF) at stimulation sites located around the brain from the heart.

Next, the signal extractor 620 may decode the collected monitoring information to extract a stimulation signal and a biosignal corresponding to the stimulation signal.

In addition, the artificial intelligence processor 630 may provide the extracted stimulation signal and biosignal as inputs of a pre-stored artificial intelligence machine learning algorithm-based stimulation control model. In addition, the artificial intelligence processor 630 may regenerate the biosignal as an output of the stimulation control model into a stimulation signal to be regulated for the balance between sympathetic and parasympathetic nerves.

For example, the artificial intelligence processor 630 may determine whether interaction between the heart and the brain or an autonomic nervous system is abnormal based on the variability of a time interval between adjacent heartbeats using heart rate variability (HRV) measured from a biosignal.

In addition, the artificial intelligence processor 630 may determine whether an autonomic nervous system is abnormal by determining a degree of maintaining blood pressure homeostasis using baroreflex sensitivity (BRS) measured from a biosignal, and regenerate a stimulation signal in real time.

For example, the artificial intelligence processor 630 may monitor a brain response by electroencephalogram (EEG) among information included in a biosignal. The artificial intelligence processor 630 may provide frontal lobe activation information according to the brain response as an input of the artificial intelligence machine learning algorithm-based stimulation control model.

As another example, among information included in a biosignal, as a result of monitoring a nerve response by photoplethysmography (PPG) measured from at least one of the ear, the neck, and the wrist, the artificial intelligence processor 630 may provide autonomic nerve information according to the nerve response as an input of an artificial intelligence machine learning algorithm-based stimulation control model.

In addition, among information included in a biosignal, as a result of monitoring a body response by physical activity measurement (Actigraph) measured from at least one of the ear, the neck, and the wrist, the artificial intelligence processor 630 may provide autonomic nerve information according to the body response as an input of the artificial intelligence machine learning algorithm-based stimulation control model.

The communicator 640 may feed back the regenerated stimulation signal to the personalized vagus nerve stimulation and pulse electromagnetic field treatment device.

Hereinafter, a method of operating a telemedicine system is described.

Figure 7:
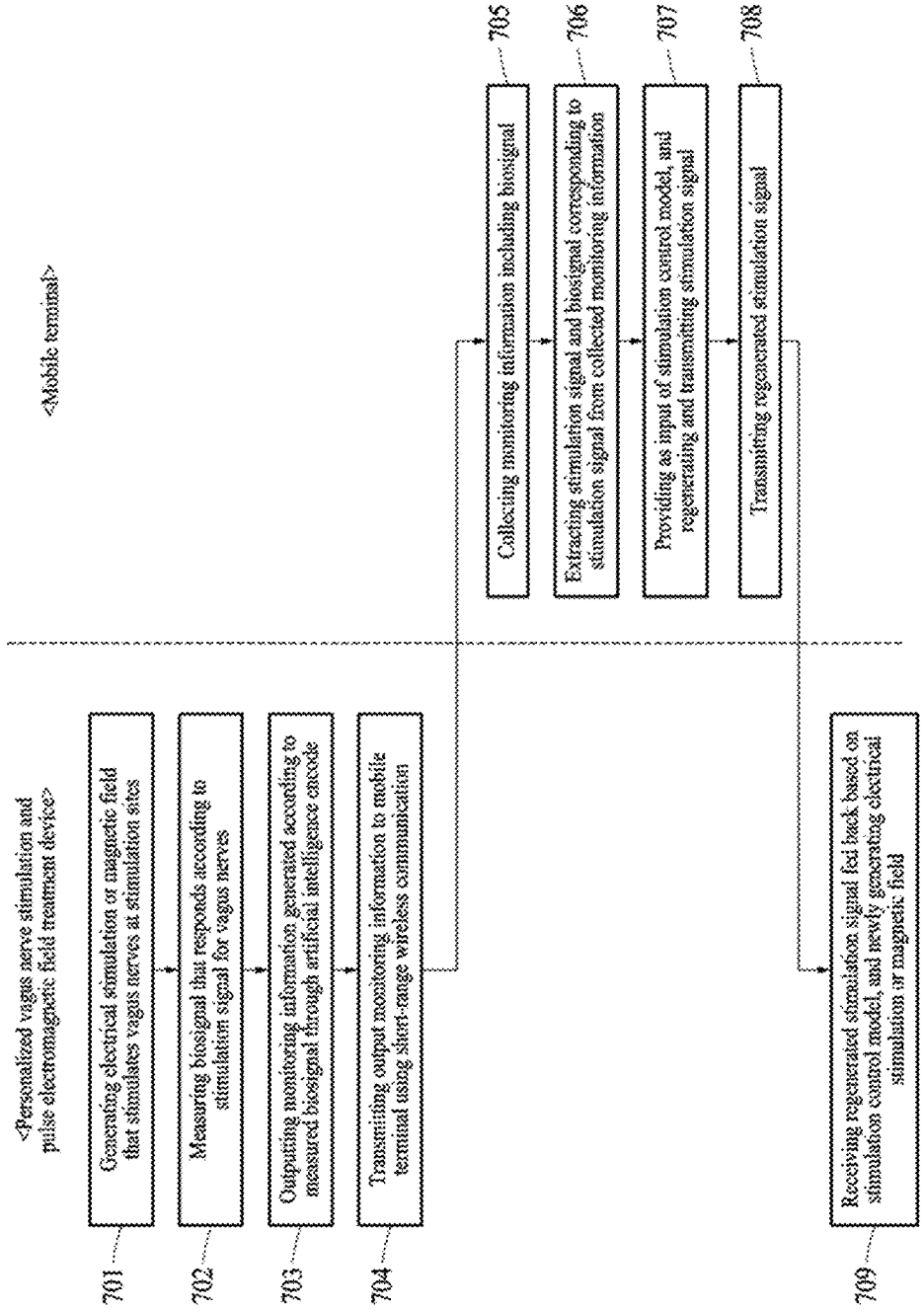
FIG. 7 is a flowchart for explaining a method of operating a telemedicine system according to one embodiment.

However, in FIG. 7, an artificial intelligence-based stimulation control model corresponds to an embodiment in which a mobile application is embedded in a mobile terminal and processed, and a stimulation control model corresponds to an embodiment processed in a cloud server.

FIG. 7 is a flowchart for explaining a method of operating a telemedicine system according to one embodiment.

In the method of operating a telemedicine system, first, electrical stimulation or a magnetic field for stimulating vagus nerves may be generated based on a stimulation signal (step 701).

For example, in the method of operating a telemedicine system, electrical stimulation may be generated in the form of cranial electrotherapy stimulation (CES) at two or more stimulation sites located on the auricle and the earlobe, respectively.

In this case, in the method of operating a telemedicine system, electrical stimulation may be generated at an intensity of 0 to 20 mA, a frequency band of 0 to 1,000 Hz, and a pulse width of 0 to 1,000 μS.

In addition, in the method of operating a telemedicine system, electrical stimulation may be generated in the form of transcutaneous electrical nerve stimulation (TENS) at two or more stimulation sites located in bilateral carotid arteries of the neck.

In this case, in the method of operating a personalized vagus nerve stimulation and pulse electromagnetic field treatment device, electrical stimulation may be generated at an intensity of 0 to 20 mA, a frequency band of 0 to 1,000 Hz, and a pulse width of 0 to 1,000 μS.

In addition, in the method of operating a telemedicine system, a magnetic field for stimulating vagus nerves may be generated based on a stimulation signal.

Next, in the method of operating a telemedicine system, a biosignal that responds to a stimulation signal for vagus nerves may be measured.

For example, in the method of operating a telemedicine system, a biosignal obtained by monitoring a brain response by electroencephalogram (EEG) may be measured.

In addition, in the method of operating a telemedicine system, a biosignal obtained by monitoring a nerve response by photoplethysmography (PPG) measured from at least one of the ear, the neck, and the wrist may be measured.

In addition, in the method of operating a telemedicine system, a biosignal obtained by monitoring a body response by physical activity measurement (Actigraph) measured from at least one of the ear, the neck, and the wrist may be measured (step 702).

In the method of operating a telemedicine system, monitoring information generated according to the measured biosignal may be output through an artificial intelligence encoder (step 703).

In the method of operating a telemedicine system, to output monitoring information through an artificial intelligence encoder, frontal lobe activation information according to a brain response may be encoded and output through an artificial intelligence encoder.

For example, in the method of operating a telemedicine system, to output monitoring information through an artificial intelligence encoder, autonomic nerve information according to a nerve response may be encoded and output through an artificial intelligence encoder.

In addition, in the method of operating a telemedicine system, to output monitoring information through an artificial intelligence encoder, movement information according to a body response may be encoded and output through an artificial intelligence encoder.

Next, in the method of operating a telemedicine system, the output monitoring information may be processed to be transmitted to a mobile terminal using short-range wireless communication (step 704).

Next, in the method of operating a telemedicine system, the monitoring information including a biosignal may be collected by a mobile terminal (step 705).

In addition, in the method of operating a telemedicine system, a stimulation signal and a biosignal in response to the stimulation signal may be extracted from the transmitted monitoring information (step 706), and the extracted stimulation signal and biosignal may be provided as inputs of a pre-stored artificial intelligence machine learning algorithm-based stimulation control model.

In addition, in the method of operating a telemedicine system, the biosignal as an output of the stimulation control model may be regenerated into a stimulation signal to be regulated for the balance between sympathetic and parasympathetic nerves (step 707), and the regenerated stimulation signal may be transmitted to the personalized vagus nerve stimulation and pulse electromagnetic field treatment device for feedback (step 708).

The personalized vagus nerve stimulation and pulse electromagnetic field treatment device may receive the regenerated stimulation signal fed back based on the stimulation control model, and may newly generate electrical stimulation or a magnetic field (step 709).

Figure 8:
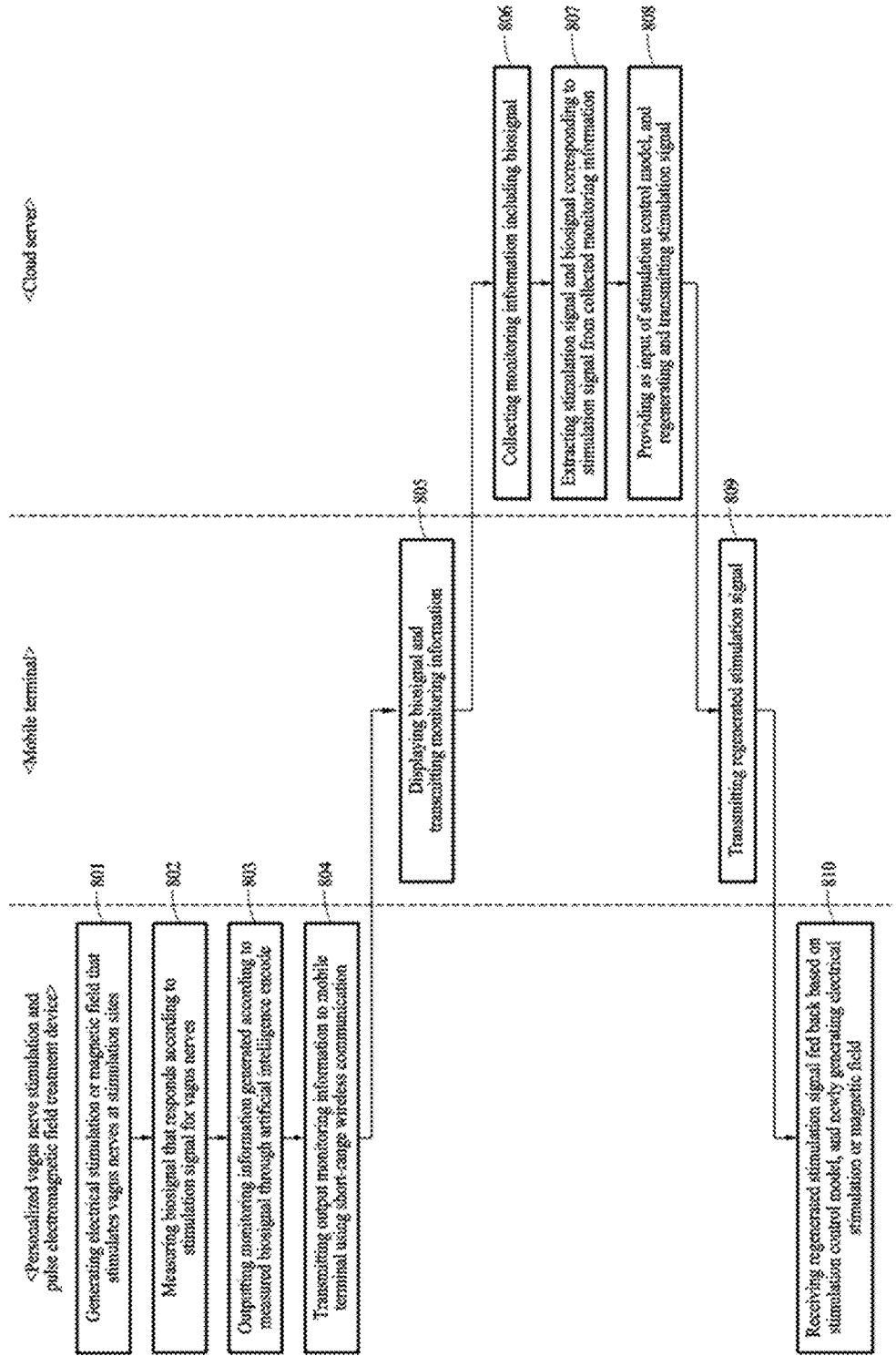
FIG. 8 is a flowchart for explaining a method of operating a telemedicine system according to one embodiment.

FIG. 8 is a flowchart for explaining a method of operating a telemedicine system according to one embodiment.

In the method of operating a telemedicine system, using the personalized vagus nerve stimulation and pulse electromagnetic field treatment device, electrical stimulation or a magnetic field for stimulating vagus nerves may be generated based on a stimulation signal (step 801).

For example, in the method of operating a telemedicine system, electrical stimulation may be generated in the form of cranial electrotherapy stimulation (CES) at two or more stimulation sites located on the auricle and the earlobe, respectively.

In this case, in the method of operating a telemedicine system, electrical stimulation may be generated at an intensity of 0 to 20 mA, a frequency band of 0 to 1,000 Hz, and a pulse width of 0 to 1,000 μS.

In addition, in the method of operating a telemedicine system, electrical stimulation may be generated in the form of transcutaneous electrical nerve stimulation (TENS) at two or more stimulation sites located in bilateral carotid arteries of the neck.

In this case, in the method of operating a personalized vagus nerve stimulation and pulse electromagnetic field treatment device, electrical stimulation may be generated at an intensity of 0 to 20 mA, a frequency band of 0 to 1,000 Hz, and a pulse width of 0 to 1,000 μS.

In addition, in the method of operating a telemedicine system, a magnetic field for stimulating vagus nerves may be generated based on a stimulation signal.

Next, in the method of operating a telemedicine system, a biosignal that responds to a stimulation signal for vagus nerves may be measured (step 802).

For example, in the method of operating a telemedicine system, a biosignal obtained by monitoring a brain response by electroencephalogram (EEG) may be measured.

In addition, in the method of operating a telemedicine system, a biosignal obtained by monitoring a nerve response by photoplethysmography (PPG) measured from at least one of the ear, the neck, and the wrist may be measured.

In addition, in the method of operating a telemedicine system, a biosignal obtained by monitoring a body response by physical activity measurement (Actigraph) measured from at least one of the ear, the neck, and the wrist may be measured.

In the method of operating a telemedicine system, monitoring information generated according to the measured biosignal may be output through an artificial intelligence encoder (step 803). To output monitoring information through an artificial intelligence encoder, frontal lobe activation information according to a brain response may be encoded and output through an artificial intelligence encoder.

For example, in the method of operating a telemedicine system, to output monitoring information through an artificial intelligence encoder, autonomic nerve information according to a nerve response may be encoded and output through an artificial intelligence encoder.

In addition, in the method of operating a telemedicine system, to output monitoring information through an artificial intelligence encoder, movement information according to a body response may be encoded and output through an artificial intelligence encoder.

Next, in the method of operating a telemedicine system, the output monitoring information may be processed to be transmitted to a mobile terminal using short-range wireless communication (step 804).

Next, the mobile terminal transmits monitoring information to a cloud server while performing an operation of displaying a biosignal through a display device (step 805).

In addition, in the method of operating a telemedicine system, the transmitted monitoring information may be collected (step 806), and a stimulation signal and a biosignal in response to the stimulation signal may be extracted from the monitoring information (step 807).

Next, the extracted stimulation signal and biosignal may be provided as inputs of a pre-stored artificial intelligence machine learning algorithm-based stimulation control model.

In addition, in the method of operating a telemedicine system, the biosignal as an output of the stimulation control model may be regenerated into a stimulation signal to be regulated for the balance between sympathetic and parasympathetic nerves (step 808), and the regenerated stimulation signal may be transmitted to the personalized vagus nerve stimulation and pulse electromagnetic field treatment device for feedback.

The mobile terminal may transmit the regenerated stimulation signal provided from the cloud server to the personalized vagus nerve stimulation and pulse electromagnetic field treatment device (step 809).

The personalized vagus nerve stimulation and pulse electromagnetic field treatment device may receive the regenerated stimulation signal fed back based on the stimulation control model, and may newly generate electrical stimulation or a magnetic field (step 810).

Figure 9:
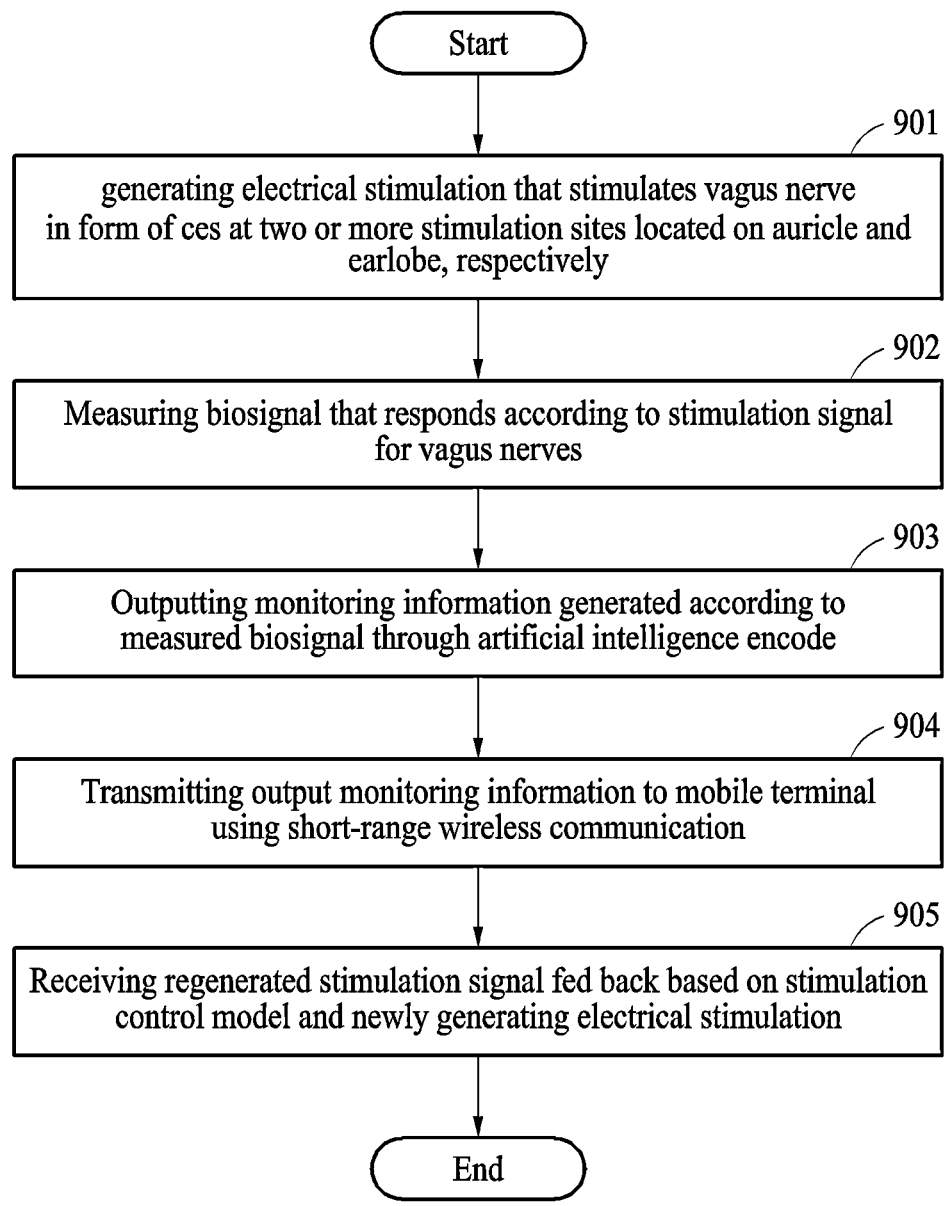

FIG. 9 is a flowchart for explaining a method of operating a personalized vagus nerve stimulation and pulse electromagnetic field treatment device according to one embodiment.

In the method of operating a personalized vagus nerve stimulation and pulse electromagnetic field treatment device, first, electrical stimulation for stimulating vagus nerves may be generated based on a stimulation signal (step 901).

For example, in the method of operating a personalized vagus nerve stimulation and pulse electromagnetic field treatment device, electrical stimulation may be generated in the form of cranial electrotherapy stimulation (CES) at two or more stimulation sites located on the auricle and the earlobe, respectively.

In the method of operating a personalized vagus nerve stimulation and pulse electromagnetic field treatment device, electrical stimulation may be generated at an intensity of 0 to 20 mA, a frequency band of 0 to 1,000 Hz, and a pulse width of 0 to 1,000 μS.

Next, in the method of operating a personalized vagus nerve stimulation and pulse electromagnetic field treatment device, a biosignal that responds to a stimulation signal for vagus nerves may be measured.

For example, in the method of operating a personalized vagus nerve stimulation and pulse electromagnetic field treatment device, a biosignal obtained by monitoring a brain response by electroencephalogram (EEG) may be measured.

In addition, in the method of operating a personalized vagus nerve stimulation and pulse electromagnetic field treatment device, a biosignal obtained by monitoring a nerve response by photoplethysmography (PPG) measured from at least one of the ear, the neck, and the wrist may be measured.

In addition, in the method of operating a personalized vagus nerve stimulation and pulse electromagnetic field treatment device, a biosignal obtained by monitoring a body response by physical activity measurement (Actigraph) measured from at least one of the ear, the neck, and the wrist may be measured.

In the method of operating a personalized vagus nerve stimulation and pulse electromagnetic field treatment device, monitoring information generated according to the measured biosignal may be output through an artificial intelligence encoder (step 903).

In the method of operating a personalized vagus nerve stimulation and pulse electromagnetic field treatment device, to output monitoring information through an artificial intelligence encoder, frontal lobe activation information according to a brain response may be encoded and output through an artificial intelligence encoder.

For example, in the method of operating a personalized vagus nerve stimulation and pulse electromagnetic field treatment device, to output monitoring information through an artificial intelligence encoder, autonomic nerve information according to a nerve response may be encoded and output through an artificial intelligence encoder.

In addition, in the method of operating a personalized vagus nerve stimulation and pulse electromagnetic field treatment device, to output monitoring information through an artificial intelligence encoder, movement information according to a body response may be encoded and output through an artificial intelligence encoder.

Next, in the method of operating a personalized vagus nerve stimulation and pulse electromagnetic field treatment device, the output monitoring information may be processed to be transmitted to a mobile terminal using short-range wireless communication (step 904).

Next, in the method of operating a personalized vagus nerve stimulation and pulse electromagnetic field treatment device, the regenerated stimulation signal fed back based on a stimulation control model may be received from a mobile terminal or a cloud server, and electrical stimulation may be newly generated (step 905).

Figure 10:
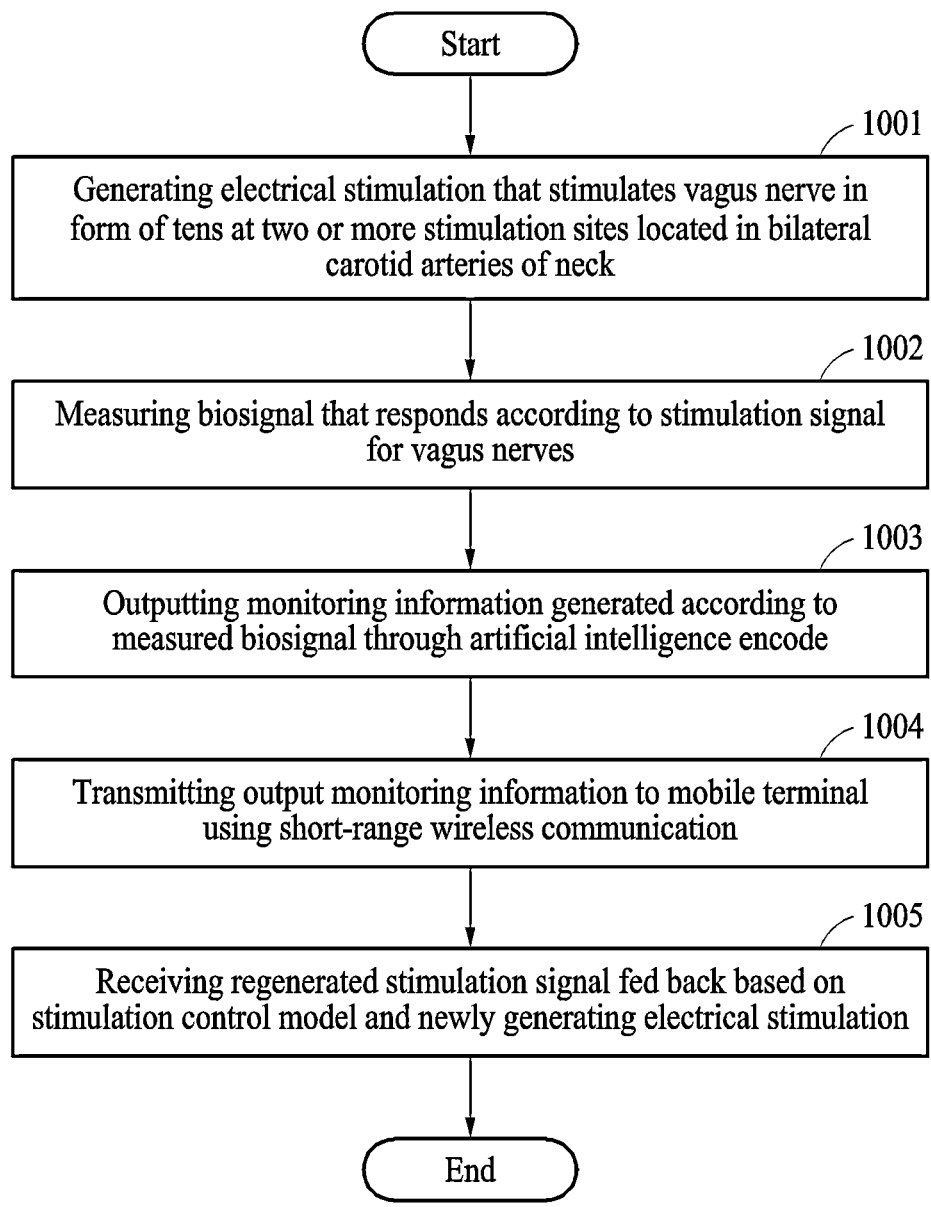

FIG. 10 is a flowchart for explaining a method of operating a personalized vagus nerve stimulation and pulse electromagnetic field treatment device according to one embodiment.

In the method of operating a personalized vagus nerve stimulation and pulse electromagnetic field treatment device, first, electrical stimulation for stimulating vagus nerves may be generated based on a stimulation signal (step 1001).

For example, in the method of operating a personalized vagus nerve stimulation and pulse electromagnetic field treatment device, electrical stimulation may be generated in the form of transcutaneous electrical nerve stimulation (TENS) at two or more stimulation sites located in bilateral carotid arteries of the neck.

In the method of operating a personalized vagus nerve stimulation and pulse electromagnetic field treatment device, electrical stimulation may be generated at an intensity of 0 to 20 mA, a frequency band of 0 to 1,000 Hz, and a pulse width of 0 to 1,000 μS.

Next, in the method of operating a personalized vagus nerve stimulation and pulse electromagnetic field treatment device, a biosignal that responds to a stimulation signal for vagus nerves may be measured.

For example, in the method of operating a personalized vagus nerve stimulation and pulse electromagnetic field treatment device, a biosignal obtained by monitoring a brain response by electroencephalogram (EEG) may be measured.

In addition, in the method of operating a personalized vagus nerve stimulation and pulse electromagnetic field treatment device, a biosignal obtained by monitoring a nerve response by photoplethysmography (PPG) measured from at least one of the ear, the neck, and the wrist may be measured.

In addition, in the method of operating a personalized vagus nerve stimulation and pulse electromagnetic field treatment device, a biosignal obtained by monitoring a body response by physical activity measurement (Actigraph) measured from at least one of the ear, the neck, and the wrist may be measured.

In the method of operating a personalized vagus nerve stimulation and pulse electromagnetic field treatment device, monitoring information generated according to the measured biosignal may be output through an artificial intelligence encoder (step 1003).

In the method of operating a personalized vagus nerve stimulation and pulse electromagnetic field treatment device, to output monitoring information through an artificial intelligence encoder, frontal lobe activation information according to a brain response may be encoded and output through an artificial intelligence encoder.

For example, in the method of operating a personalized vagus nerve stimulation and pulse electromagnetic field treatment device, to output monitoring information through an artificial intelligence encoder, autonomic nerve information according to a nerve response may be encoded and output through an artificial intelligence encoder.

In addition, in the method of operating a personalized vagus nerve stimulation and pulse electromagnetic field treatment device, to output monitoring information through an artificial intelligence encoder, movement information according to a body response may be encoded and output through an artificial intelligence encoder.

Next, in the method of operating a personalized vagus nerve stimulation and pulse electromagnetic field treatment device, the output monitoring information may be processed to be transmitted to a mobile terminal using short-range wireless communication (step 1004).

Next, in the method of operating a personalized vagus nerve stimulation and pulse electromagnetic field treatment device, the regenerated stimulation signal fed back based on a stimulation control model may be received from a mobile terminal or a cloud server, and electrical stimulation may be newly generated (step 1005).

FIG. 11 is a flowchart for explaining a method of operating a personalized vagus nerve stimulation and pulse electromagnetic field treatment device according to one embodiment.

In the method of operating a personalized vagus nerve stimulation and pulse electromagnetic field treatment device, first, a magnetic field for stimulating vagus nerves may be generated based on a stimulation signal (step 1101).

Next, in the method of operating a personalized vagus nerve stimulation and pulse electromagnetic field treatment device, a biosignal that responds to a stimulation signal for vagus nerves may be measured.

For example, in the method of operating a personalized vagus nerve stimulation and pulse electromagnetic field treatment device, a biosignal obtained by monitoring a brain response by electroencephalogram (EEG) may be measured.

In addition, in the method of operating a personalized vagus nerve stimulation and pulse electromagnetic field treatment device, a biosignal obtained by monitoring a nerve response by photoplethysmography (PPG) measured from at least one of the ear, the neck, and the wrist may be measured.

In addition, in the method of operating a personalized vagus nerve stimulation and pulse electromagnetic field treatment device, a biosignal obtained by monitoring a body response by physical activity measurement (Actigraph) measured from at least one of the ear, the neck, and the wrist may be measured.

In the method of operating a personalized vagus nerve stimulation and pulse electromagnetic field treatment device, monitoring information generated according to the measured biosignal may be output through an artificial intelligence encoder (step 1103).

In the method of operating a personalized vagus nerve stimulation and pulse electromagnetic field treatment device, to output monitoring information through an artificial intelligence encoder, frontal lobe activation information according to a brain response may be encoded and output through an artificial intelligence encoder.

For example, in the method of operating a personalized vagus nerve stimulation and pulse electromagnetic field treatment device, to output monitoring information through an artificial intelligence encoder, autonomic nerve information according to a nerve response may be encoded and output through an artificial intelligence encoder.

In addition, in the method of operating a personalized vagus nerve stimulation and pulse electromagnetic field treatment device, to output monitoring information through an artificial intelligence encoder, movement information according to a body response may be encoded and output through an artificial intelligence encoder.

Next, in the method of operating a personalized vagus nerve stimulation and pulse electromagnetic field treatment device, the output monitoring information may be processed to be transmitted to a mobile terminal using short-range wireless communication (step 1104).

Next, in the method of operating a personalized vagus nerve stimulation and pulse electromagnetic field treatment device, the regenerated stimulation signal fed back based on a stimulation control model may be received from a mobile terminal or a cloud server, and a magnetic field may be newly generated (step 1105).

As a result, when the present invention is used, a personalized medical service capable of managing symptoms anytime, anywhere based on artificial intelligence-based personalized biofeedback through digital therapeutics during daily life may be provided.

In addition, a telemedicine service delivery system in preparation for the post-corona era may be provided. Subjective processing may be eliminated through artificial intelligence stimulation feedback by monitoring an autonomic nervous system response, and a stimulation recipe optimized for a user may be provided.

In addition, by using the present invention, release of inhibitory neurotransmitters including GABA, serotonin, and norepinephrine within the central nervous system may be induced by stimulating vagus nerves. Thus, sleep disturbance, emotional disturbance, and digestive symptoms caused by an imbalance of sympathetic and parasympathetic nerves may be alleviated, and diseases or related symptoms caused by an imbalance between sympathetic and parasympathetic nerves may be alleviated.

In addition, overactivation of sympathetic nerves due to chronic pain/stress and affective disorders may be corrected. The limitations of conventional vagus nerve stimulators provided based on manuals may be overcome through personalized vagus nerve stimulation optimization using an artificial intelligence algorithm.

In addition, the parasympathetic nervous system may be activated for body and mind relaxation. By enhancing metabolism of fibroblasts, chondrocytes, and osteoblasts through magnetic field stimulation and modulating the effects of hormones and neurotransmitters on the receptors of various cells, low back pain, pelvic pain, neuropathic pain, and neuralgia/myalgia may be alleviated, and the treatment effect of fractures may be increased.

The apparatus described above may be implemented as a hardware component, a software component, and/or a combination of hardware components and software components. For example, the apparatus and components described in the embodiments may be achieved using one or more general purpose or special purpose computers, such as, for example, a processor, a controller, an arithmetic logic unit (ALU), a digital signal processor, a microcomputer, a field programmable array (FPA), a programmable logic unit (PLU), a microprocessor, or any other device capable of executing and responding to instructions. The processing device may execute an operating system (OS) and one or more software applications executing on the operating system. In addition, the processing device may access, store, manipulate, process, and generate data in response to execution of the software. For ease of understanding, the processing apparatus may be described as being used singly, but those skilled in the art will recognize that the processing apparatus may include a plurality of processing elements and/or a plurality of types of processing elements. For example, the processing apparatus may include a plurality of processors or one processor and one controller. Other processing configurations, such as a parallel processor, are also possible.

The software may include computer programs, code, instructions, or a combination of one or more of the foregoing, configure the processing apparatus to operate as desired, or command the processing apparatus, either independently or collectively. In order to be interpreted by a processing device or to provide instructions or data to a processing device, the software and/or data may be embodied permanently or temporarily in any type of a machine, a component, a physical device, a virtual device, a computer storage medium or device, or a transmission signal wave. The software may be distributed over a networked computer system and stored or executed in a distributed manner. The software and data may be stored in one or more computer-readable recording media.

The methods according to the embodiments of the present invention may be implemented in the form of a program command that can be executed through various computer means and recorded in a computer-readable medium. The computer-readable medium can store program commands, data files, data structures or combinations thereof. The program commands recorded in the medium may be specially designed and configured for the present invention or be known to those skilled in the field of computer software. Examples of a computer-readable recording medium include magnetic media such as hard disks, floppy disks and magnetic tapes, optical media such as CD-ROMs and DVDs, magneto-optical media such as floptical disks, or hardware devices such as ROMs, RAMs and flash memories, which are specially configured to store and execute program commands Examples of the program commands include machine language code created by a compiler and high-level language code executable by a computer using an interpreter and the like. The hardware devices described above may be configured to operate as one or more software modules to perform the operations of the embodiments, and vice versa.

Although the present invention has been described with reference to limited embodiments and drawings, it should be understood by those skilled in the art that various changes and modifications may be made therein. For example, the described techniques may be performed in a different order than the described methods, and/or components of the described systems, structures, devices, circuits, etc., may be combined in a manner that is different from the described method, or appropriate results may be achieved even if replaced by other components or equivalents.

Therefore, other embodiments, other examples, and equivalents to the claims are within the scope of the following claims.

The invention claimed is:

1. A telemedicine system, comprising:
    a gateway for transmitting monitoring information comprising a stimulation signal and a biosignal corresponding to the stimulation signal to a cloud; and
    a server for extracting the stimulation signal and the biosignal from the transmitted monitoring information, providing the extracted stimulation signal and biosignal as inputs of a pre-stored artificial intelligence machine learning algorithm-based stimulation control model, regenerating the biosignal as an output of the stimulation control model into a stimulation signal to be regulated for balance between sympathetic and parasympathetic nerves, and feeding back the regenerated stimulation signal to a personalized vagus nerve stimulation and pulse electromagnetic field treatment device,
    wherein the monitoring information comprises a biosignal measured when vagus nerves are stimulated in a form of electromagnetism at a stimulation site based on a stimulation signal generated from the personalized vagus nerve stimulation and pulse electromagnetic field treatment device, and
    the personalized vagus nerve stimulation and pulse electromagnetic field treatment device newly stimulates vagus nerve with the feedback stimulation signal.

2. The telemedicine system according to claim 1, further comprising a medical staff terminal for outputting information comprising at least one of the measured biosignal and the regenerated stimulation signal,
    wherein the regenerated stimulation signal is updated based on electroceutical prescription information generated according to the information output from the medical staff terminal.

3. A method of operating the telemedicine system of claim 1, comprising:
    a step of generating, based on a stimulation signal, through a personalized vagus nerve stimulation and pulse electromagnetic field treatment device, at least one of electrical stimulation that stimulates vagus nerves in a form of cranial electrotherapy stimulation (CES) at two or more stimulation sites located on an auricle and an earlobe, respectively, electrical stimulation that stimulates vagus nerves in a form of transcutaneous electrical nerve stimulation (TENS) at two or more stimulation sites located in bilateral carotid arteries of a neck, and a magnetic field that stimulates vagus nerves in a form of pulsed electromagnetic field (PEMF) at stimulation sites located around a brain from a heart;
    a step of measuring a biosignal in response to the stimulation;
    a step of transmitting monitoring information comprising the measured biosignal to a gateway;
    a step of extracting, by a server, the stimulation signal and a biosignal that responds according to the stimulation signal from monitoring information transmitted through the gateway;
    a step of providing the extracted stimulation signal and biosignal as inputs of a pre-stored artificial intelligence machine learning algorithm-based stimulation control model;
    a step of regenerating the biosignal as an output of the stimulation control model into a stimulation signal to be regulated for balance between sympathetic and parasympathetic nerves; and
    a step of feeding back the regenerated stimulation signal to the personalized vagus nerve stimulation and pulse electromagnetic field treatment device,
    wherein the personalized vagus nerve stimulation and pulse electromagnetic field treatment device newly stimulates vagus nerves with the feedback stimulation signal.

4. The method according to claim 3, further comprising a step of outputting, by a medical staff terminal, information comprising at least one of the measured biosignal and the regenerated stimulation signal; and
    a step of updating the regenerated stimulation signal based on electroceutical prescription information generated according to the information output by the medical staff terminal.

5. A personalized vagus nerve stimulation and pulse electromagnetic field treatment device, comprising:
    a stimulator for generating, based on a stimulation signal, at least one of electrical stimulation that stimulates vagus nerves in a form of cranial electrotherapy stimulation (CES) at two or more stimulation sites located on an auricle and an earlobe, respectively, electrical stimulation that stimulates vagus nerves in a form of transcutaneous electrical nerve stimulation (TENS) at two or more stimulation sites located in bilateral carotid arteries of a neck, and a magnetic field that stimulates vagus nerves in a form of pulsed electromagnetic field (PEMF) at stimulation sites located around a brain from a heart;
    a biosignal monitor for measuring a biosignal that responds to stimulation applied to the vagus nerve and outputting monitoring information comprising the stimulation signal and the biosignal through an artificial intelligence encoder; and
    a communicator for transmitting the output monitoring information to a mobile terminal or a server using short-range wireless communication,
    wherein the stimulator receives a regenerated stimulation signal fed back from the mobile terminal or the server based on a stimulation control model and regenerates electrical stimulation or a magnetic field.

6. The personalized vagus nerve stimulation and pulse electromagnetic field treatment device according to claim 5, wherein the stimulation control model determines whether interaction between a heart and a brain or an autonomic nervous system is abnormal based on variability of a time interval between adjacent heartbeats using heart rate variability (HRV) measured from the biosignal, or determines whether the autonomic nervous system is abnormal by determining a degree of maintaining blood pressure homeostasis using baroreflex sensitivity (BRS) measured from the biosignal, and regenerates the stimulation signal in real time.

7. The personalized vagus nerve stimulation and pulse electromagnetic field treatment device according to claim 5, wherein the biosignal monitor monitors a brain response by electroencephalogram (EEG) as the biosignal, and encodes and outputs frontal lobe activation information according to the brain response through an artificial intelligence encoder.

8. The personalized vagus nerve stimulation and pulse electromagnetic field treatment device according to claim 5, wherein the biosignal monitor monitors a nerve response by photoplethysmography (PPG) measured from at least one of an ear, a neck, and a wrist as the biosignal, and encodes and outputs autonomic nerve information according to the nerve response through an artificial intelligence encoder.

9. The personalized vagus nerve stimulation and pulse electromagnetic field treatment device according to claim 5, wherein the biosignal monitor monitors a body response by physical activity measurement (Actigraph) measured from at least one of an ear, a neck, and a wrist as the biosignal, and encodes and outputs movement information according to the body response through an artificial intelligence encoder.

10. The personalized vagus nerve stimulation and pulse electromagnetic field treatment device according to claim 5, wherein the stimulator generates electrical stimulation at an intensity of 0 to 20 mA, a frequency band of 0 to 1,000 Hz, and a pulse width of 0 to 1,000 μS or a magnetic field at a frequency band of 0 to 1,000 Hz and a pulse width of 0 to 1,000 μS.

11. The personalized vagus nerve stimulation and pulse electromagnetic field treatment device according to claim 5, wherein the mobile terminal transmits the output monitoring information to a server,
the server extracts the stimulation signal and a biosignal that responds according to the stimulation signal from the transmitted monitoring information, provides the extracted stimulation signal and biosignal as inputs of a pre-stored artificial intelligence machine learning algorithm-based stimulation control model, regenerates the biosignal as an output of the stimulation control model into a stimulation signal to be regulated for balance between sympathetic and parasympathetic nerves, and feeds back the regenerated stimulation signal to the communicator, and
the stimulator newly generates electrical stimulation or a magnetic field as the feedback stimulation signal.

12. The personalized vagus nerve stimulation and pulse electromagnetic field treatment device according to claim 5, wherein the mobile terminal extracts the stimulation signal and a biosignal that responds according to the stimulation signal from the output monitoring information, provides the extracted stimulation signal and biosignal as inputs of a pre-stored artificial intelligence machine learning algorithm-based stimulation control model, regenerates the biosignal as an output of the stimulation control model into a stimulation signal to be regulated for balance between sympathetic and parasympathetic nerves, and feeds back the regenerated stimulation signal to the communicator, and
the stimulator newly generates electrical stimulation or a magnetic field as the feedback stimulation signal.

13. The personalized vagus nerve stimulation and pulse electromagnetic field treatment device according to claim 5, wherein the mobile terminal downloads or periodically updates the stimulation control model from the server.

14. A server, comprising:
a monitoring information collector for collecting monitoring information comprising a biosignal measured when a stimulation signal is generated from a personalized vagus nerve stimulation and pulse electromagnetic field treatment device, and at least one of stimulation of vagus nerves in a form of cranial electrotherapy stimulation (CES) at two or more stimulation sites located on an auricle and an earlobe, respectively, stimulation of vagus nerves in a form of transcutaneous electrical nerve stimulation (TENS) at two or more stimulation sites located in bilateral carotid arteries of a neck, and a magnetic field that stimulates vagus nerves in a form of pulsed electromagnetic field (PEMF) at stimulation sites located around a brain from a heart is generated;
a signal extractor for extracting the stimulation signal and a biosignal corresponding to the stimulation signal from the collected monitoring information;
an artificial intelligence processor for providing the extracted stimulation signal and biosignal as inputs of a pre-stored artificial intelligence machine learning algorithm-based stimulation control model, and regenerating the biosignal as an output of the stimulation control model into a stimulation signal to be regulated for balance between sympathetic and parasympathetic nerves; and
a communicator for performing control to feed back the regenerated stimulation signal to the personalized vagus nerve stimulation and pulse electromagnetic field treatment device.

15. The server according to claim 14, wherein the artificial intelligence processor determines whether interaction between a heart and a brain or an autonomic nervous system is abnormal based on variability of a time interval between adjacent heartbeats using heart rate variability (HRV) measured from the biosignal, or
determines whether the autonomic nervous system is abnormal by determining a degree of maintaining blood pressure homeostasis using baroreflex sensitivity (BRS) measured from the biosignal, and regenerates the stimulation signal in real time.

16. The server according to claim 14, wherein, among information comprised in the biosignal, as a result of monitoring a brain response by electroencephalogram (EEG), the artificial intelligence processor provides frontal lobe activation information according to the brain response as an input of the artificial intelligence machine learning algorithm-based stimulation control model.

17. The server according to claim 14, wherein, among information comprised in the biosignal, as a result of monitoring a nerve response by photoplethysmography (PPG) measured from at least one of an ear, a neck, and a wrist, the artificial intelligence processor provides autonomic nerve information according to the nerve response as an input of the artificial intelligence machine learning algorithm-based stimulation control model.

18. The server according to claim 14, wherein, among information comprised in the biosignal, as a result of monitoring a body response by physical activity measurement (Actigraph) measured from at least one of an ear, a neck, and a wrist, the artificial intelligence processor provides autonomic nerve information according to the body response as an input of the artificial intelligence machine learning algorithm-based stimulation control model.

\* \* \* \* \*